(12) United States Patent
Ikemoto et al.

(10) Patent No.: US 6,649,761 B2
(45) Date of Patent: Nov. 18, 2003

(54) PROCESS FOR PREPARING PIPERAZINEPENTANEAMIDE HIV PROTEASE INHIBITORS

(75) Inventors: Norihiro Ikemoto, Edison, NJ (US); Jinchu Liu, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/158,527

(22) Filed: May 30, 2002

(65) Prior Publication Data

US 2003/0144512 A1 Jul. 31, 2003

Related U.S. Application Data

(60) Provisional application No. 60/294,362, filed on May 30, 2001.

(51) Int. Cl.[7] ........................ C07D 413/06; C07D 413/14
(52) U.S. Cl. ........................ 544/364; 544/238; 544/295; 544/357; 544/367; 544/369; 562/89
(58) Field of Search ........................ 544/238, 295, 544/357, 364, 367, 369

(56) References Cited

U.S. PATENT DOCUMENTS 5,382,584 A * 1/1995 Balasubramanian ........ 514/252

FOREIGN PATENT DOCUMENTS

| WO | WO 01/38332 | 5/2001 |
| WO | 02/096359 A2 * | 12/2002 |

* cited by examiner

Primary Examiner—Emily Bernhardt
(74) Attorney, Agent, or Firm—Kenneth R. Walton; Valerie J. Camara

(57) ABSTRACT

A process for preparing γ-hydroxy-4-[[2-oxazolyl]alkyl]-α-[(cyclo)alkyl- or aryl- or heteroaryl-substituted methyl]-2-[[(un)substituted alkyl]aminocarbonyl]-1-piperazinepentanamides is disclosed. The piperazinepentanamides are useful as HIV protease inhibitors. A process for making a 4-[[2-oxazolyl]alkyl]-2-[[(un)substituted alkyl]aminocarbonyl]piperazine by treating a ketoamide precursor with fuming sulfuric acid in the presence of polyphosphoric acid is also disclosed. In addition, a process for enhancing the optical purity of 4-[[2-oxazolyl]alkyl]-2-[[(un)substituted alkyl]aminocarbonyl]-piperazines via the formation 2-naphthalenesulfonic acid crystal salts thereof is disclosed, as well as a method for purifying 2-naphthalenesulfonic acid.

15 Claims, No Drawings

PROCESS FOR PREPARING PIPERAZINEPENTANEAMIDE HIV PROTEASE INHIBITORS

This application claims the benefit of U.S. Provisional Application No. 60/294,362, filed May 30, 2001, the disclosure of which is hereby incorporated by reference in its entirety.

FIELD OF THE INVENTION

The present invention is directed to the synthesis of γ-hydroxy-4-[[2-oxazolyl]alkyl]-α-[(cyclo)alkyl- or aryl- or heteroaryl-substituted methyl]-2-[[(un)substituted alkyl] aminocarbonyl]-1-piperazinepentanamides which are HIV protease inhibitors. The present invention also includes the preparation of intermediates useful in the synthesis of the piperazinepentanamide HIV protease inhibitors.

BACKGROUND OF THE INVENTION

The HIV retrovirus is the causative agent for AIDS. The HIV-1 retrovirus primarily uses the CD4 receptor (a 58 kDa transmembrane protein) to gain entry into cells, through high-affinity interactions between the viral envelope glycoprotein (gp 120) and a specific region of the CD4 molecule found in T-lymphocytes and CD4 (+) T-helper cells (Lasky L. A. et al., *Cell* 1987, 50: 975–985). HIV infection is characterized by an asymptomatic period immediately following infection that is devoid of clinical manifestations in the patient. Progressive HIV-induced destruction of the immune system then leads to increased susceptibility to opportunistic infections, which eventually produces a syndrome called AIDS-related complex (ARC) characterized by symptoms such as persistent generalized lymphadenopathy, fever, and weight loss, followed itself by full blown AIDS.

As in the case of several other retroviruses, HIV encodes the production of a protease which carries out post-translational cleavage of precursor polypeptides in a process necessary for the formation of infectious virions (S. Crawford et al., *J. Virol.* 1985, 53: 899). These gene products include pol—which encodes the virion RNA-dependent DNA polymerase (reverse transcriptase), an endonuclease, and HIV protease—and gag—which encodes the core-proteins of the virion. (H. Toh et al., *EMBO J.* 1985, 4: 1267; L. H. Pearl et al., *Nature* 1987, 329–351; M. D. Power et al., *Science* 1986, 231: 1567).

A number of synthetic anti-viral agents targeted to various stages in the replication cycle of HIV have been disclosed. These agents include inhibitors of HIV cellular fusion (Turpin et al., *Expert Opinion on Therapeutic Patents* 2000, 10: 1899–1909), reverse transcriptase inhibitors (e.g., didanosine, zidovudine (AZT), and efavirenz), integrase inhibitors (Neamati, *Expert Opinion on Investigational Drugs* 2000, 10: 281–296), and protease inhibitors (e.g., indinavir, ritonavir, and saquinavir). Protease inhibitors inhibit the formation of infectious virions by interfering with the processing of viral polyprotein precursors. Processing of these precursor proteins requires the action of virus-encoded proteases which are essential for replication (Kohl, N. E. et al., *Proc. Natl. Acad. Sci. USA* 1988, 85: 4686).

A substantial and persistent problem in the treatment of AIDS has been the ability of the HIV virus to develop resistance to the therapeutic agents employed to treat the disease. Resistance to HIV-1 protease inhibitors has been associated with 25 or more amino acid substitutions in both the protease and the cleavage sites. Many of these viral variants are resistant to all of the HIV protease inhibitors currently in clinical use. See Condra et al., *Drug Resistance Updates* 1998, 1: 1–7; Condra et al., *Nature* 1995, 374: 569–571; Condra et al., *J. Virol.* 1996, 70:8270–8276; Patrick et al., *Antiviral Ther.* 1996, Suppl. 1: 17–18; and Tisdale et al., *Antimicrob. Agents Chemother.* 1995, 39: 1704–1710.

Certain γ-hydroxy-4-[[2-oxazolyl]alkyl]-α-[substituted methyl]-2-[[(fluoroalkyl)amino]carbonyl]-1-piperazinepentanamides are HIV protease inhibitors which are much more potent against HIV viral mutants than protease inhibitors presently in clinical use. The synthesis of these compounds is a complicated, multi-step process having a relatively low overall yield. The synthesis of these compounds can be represented by Scheme A as follows, wherein A10 represents the desired piperazinepentaneamide HIV protease inhibitor:

SCHEME A

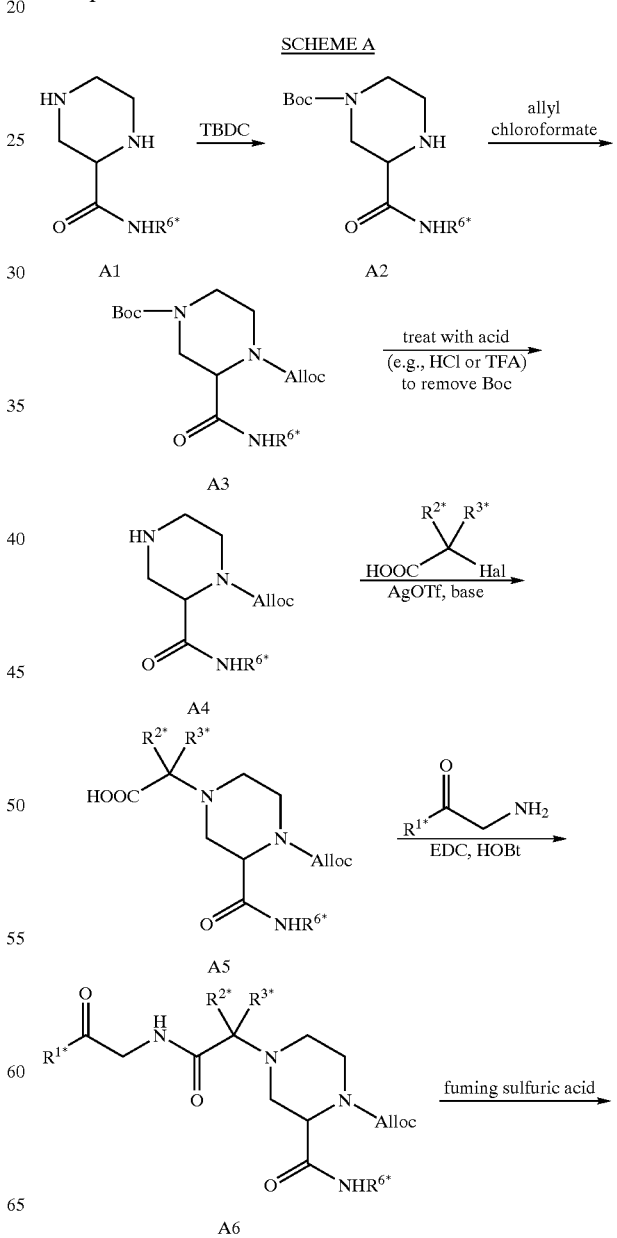

-continued

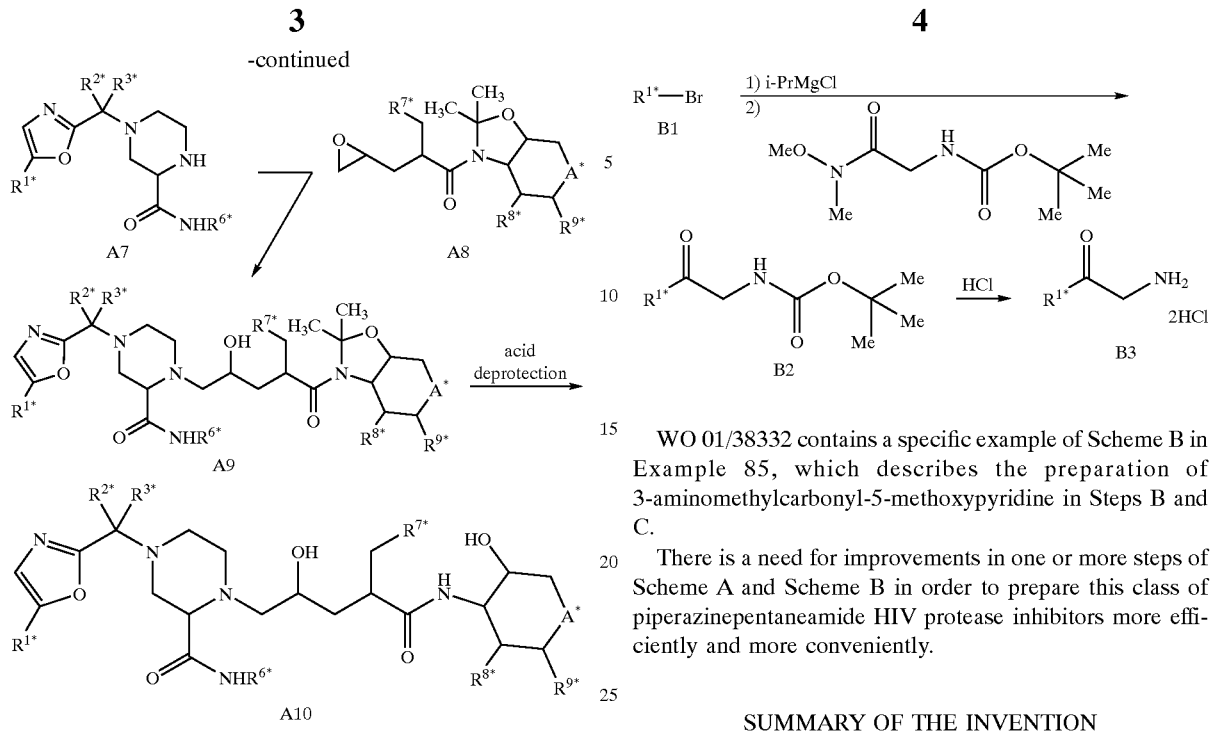

A*=absent, CH$_2$, or O;

R$^{1*}$=aryl or heteroaryl, wherein aryl is optionally substituted with one or more of halogen, hydroxy, cyano, alkyl, fluoroalkyl, alkoxy, fluoroalkoxy, S-alkyl, amino, or heteroaryl; and heteroaryl is optionally substituted with one or more of halogen, hydroxy, cyano, alkyl, fluoroalkyl, alkoxy, fluoroalkoxy, S-alkyl, amino, aryl, or heteroaryl.

R$^{2*}$, R$^{3*}$=H or alkyl; or

R$^2$ * and R$^3$ * together with the carbon to which they are attached form cycloalkyl;

R$^{6*}$=monofluoroalkyl or polyfluoroalkyl;

R$^{7*}$=alkyl, cycloalkyl, aryl or heteroaryl, wherein aryl is optionally substituted with one or more of halogen, OH, alkyl, alkenyl, alkynyl, fluoroalkyl, alkoxy, or heteroaryl; and heteroaryl is optionally substituted with one or more of halogen, OH, alkyl, alkenyl, alkynyl, fluoroalkyl, alkoxy, or aryl;

R$^{8*}$, R$^{9*}$=H, OH, alkyl, fluoroalkyl, or alkoxy; or

R$^{8*}$ and R$^{9*}$ together with the carbons to which they are attached form a fused benzene ring.

WO 01/38332 presents a specific example of Scheme A in Example 85, which describes the preparation of (αR,γS,2S)-N-[(3S,4S)-3,4-dihydro-3-hydroxy-2H-1-benzopyran-4-yl]-γ-hydroxy-4-[1-[5-(5-methoxy-3-pyridinyl)-2-oxazolyl]-1-methylethyl]-α-(phenylmethyl)-2-[[(2,2,2-trifluoroethyl)amino]carbonyl]-1-piperazinepentanamide (hereinafter alternatively referred to as Compound 26).

The preparation of the ketoamines of formula R$^{1*}$—C(=O)CH$_2$NH$_2$ employed in Scheme A to make Compound A6 can be represented by Scheme B as follows:

WO 01/38332 contains a specific example of Scheme B in Example 85, which describes the preparation of 3-aminomethylcarbonyl-5-methoxypyridine in Steps B and C.

There is a need for improvements in one or more steps of Scheme A and Scheme B in order to prepare this class of piperazinepentaneamide HIV protease inhibitors more efficiently and more conveniently.

SUMMARY OF THE INVENTION

The present invention provides for improvements in the process for preparing γ-hydroxy-4-[[2-oxazolyl]alkyl]-α-[(cyclo)alkyl- or aryl- or heteroaryl-substituted methyl]-2-[[(un)substituted alkyl]aminocarbonyl]-1-piperazinepentanamides. The present invention includes an improved process for making a 4-[[2-oxazolyl]alkyl]-2-[[(un)substituted alkyl]aminocarbonyl]piperazine by treating a ketoamide precursor with fuming sulfuric acid in the presence of polyphosphoric acid. The present invention also includes a process for enhancing the optical purity of 4-[[2-oxazolyl]alkyl]-2-[[(un)substituted alkyl]aminocarbonyl]-piperazines via the formation 2-naphthalenesulfonic acid crystal salts thereof. The present invention further includes a method for purifying 2-naphthalenesulfonic acid.

The foregoing embodiments as well as other embodiments, aspects and features of the present invention are either further described in or will be apparent from the ensuing description, examples, and appended claims.

DETAILED DESCRIPTION OF THE INVENTION

The present invention includes a process for preparing a piperazine of Formula (II):

(II)

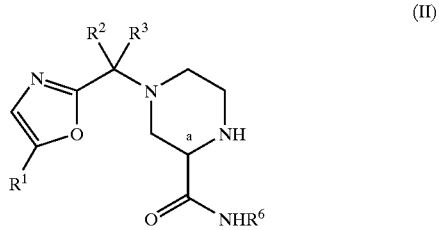

which comprises:
(A) treating a ketoamide of Formula (I):

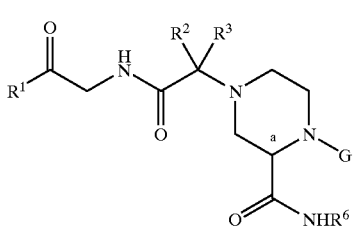

with fuming sulfuric acid in the presence of polyphosphoric acid to obtain the piperazine II; wherein stereocenter a is either in the R configuration or in the S configuration;
G is a nitrogen-protecting group;
$R^1$ is:

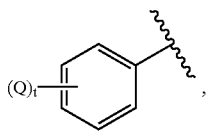

heterocycle, or substituted heterocycle;
wherein each Q is independently hydrogen, cyano, $C_1-C_4$ alkyl, or —O—$C_1-C_4$ alkyl;
heterocycle in $R^1$ is:

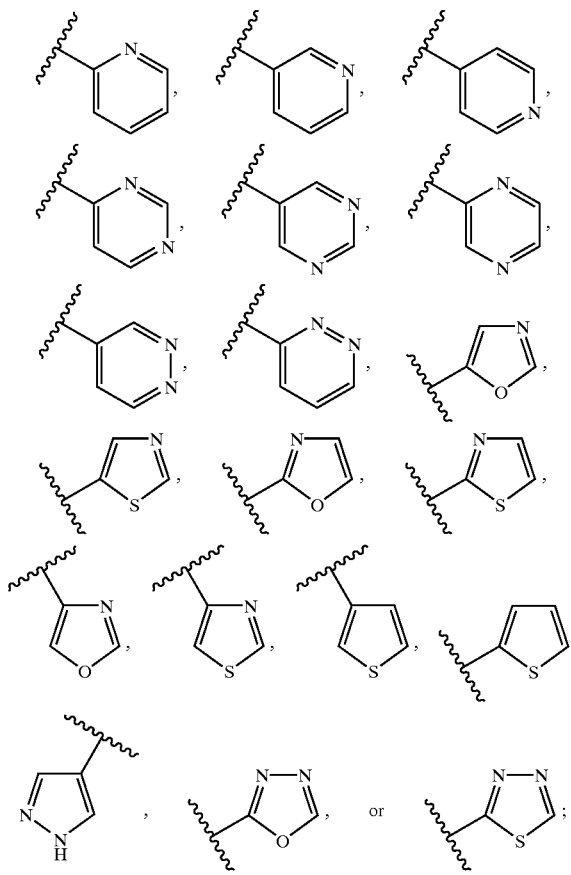

substituted heterocycle in $R^1$ is a heterocycle as defined above with one or more substituents (e.g., from 1 to 4 substituents, or from 1 to 3 substituents; or is di-substituted; or is mono-substituted) independently selected from cyano, $C_1-C_4$ alkyl, —O—$C_1-C_4$ alkyl, S—($C_1-C_4$ alkyl), $NR^aR^b$, thiazolyl, oxazolyl, imidazolyl, pyrazolyl, triazolyl, pyrrolyl, isoxazolyl, and isothiazolyl;

$R^2$ and $R^3$ are each independently hydrogen, $C_1-C_6$ alkyl, or aryl, wherein the alkyl group is optionally substituted with one or more substituents (e.g., from 1 to 6, or from 1 to 5, or from 1 to 4, or from 1 to 3 substituents; or is di-substituted; or is mono-substituted) each of which is independently halogen, —O—$C_1-C_6$ alkyl, or —O—$C_1-C_6$ haloalkyl; and wherein the aryl group is optionally substituted with one or more substituents each of which is independently halogen, —$C_1-C_6$ alkyl, —$C_1-C_6$ haloalkyl, —O—$C_1-C_6$ alkyl, or —O—$C_1-C_6$ haloalkyl; or $R^2$ and $R^3$ together with the carbon to which they are attached form $C_3-C_8$ cycloalkyl which is optionally substituted with one or more substituents (e.g., from 1 to 6, or from 1 to 5, or from 1 to 4, or from 1 to 3 substituents; or is di-substituted; or is mono-substituted) each of which is independently halogen, —$C_1-C_6$ alkyl, —$C_1-C_6$ haloalkyl, —O—$C_1-C_6$ alkyl, —O—$C_1-C_6$ haloalkyl, or —$C_1-C_6$ alkyl substituted with —O—$C_1-C_6$ alkyl;

$R^6$ is —H or $C_1-C_6$ alkyl optionally substituted with one or more substituents (e.g., from 1 to 6, or from 1 to 5, or from 1 to 4, or from 1 to 3 substituents; or is di-substituted; or is mono-substituted) each of which is independently
(1) halogen,
(2) —O—$C_1-C_6$ alkyl,
(3) —O—$C_1-C_6$ haloalkyl,
(4) —$C_1-C_6$ alkyl substituted with —$C_1-C_6$ alkyl,
(5) —$N(R^c)_2$,
(6) —$CO_2R^c$,
(7) —$N(R^c)(SO_2R^c)$,
(8) —C(=O)$R^c$, or
(9) —C(=O)—$N(R^c)_2$;

$R^a$ and $R^b$ are each independently —H or —$C_1-C_4$ alkyl; or alternatively $R^a$ and $R^b$ together with the nitrogen to which they are attached form $C_1-C_6$ azacycloalkyl;
each $R^c$ is independently —H or —$C_1-C_4$ alkyl; and
t is an integer equal to zero, 1 or 2.

In the definition of stereocenter a in the above process, it is to be understood that stereocenter a is either wholly or substantially in the R or the S configuration. The term "substantially" means that the ketoamide I reactant generally has at least about a 20% enantiomeric excess (ee) of the desired configuration over the other, typically has at least about a 40% ee, and more typically has at least an 80% ee of one configuration over the other at stereocenter a. Ketoamide I often has a 90% to 99% ee, or even has 100% ee, of one configuration over the other. In one embodiment of the process, ketoamide I is in the S configuration at stereocenter a; i.e., ketoamide I is wholly or substantially in the S configuration.

In an embodiment of the process of the invention, $R^1$ is as originally defined, except that $R^a$ and $R^b$ are each independently —H or —$C_1-C_4$ alkyl. In other embodiments, $R^1$ is as originally defined, except that $R^a$ and $R^b$ are both —H; or $R^a$ and $R^b$ are each a —$C_1-C_4$ alkyl; or $R^a$ and $R^b$ are each independently —H, methyl, or ethyl; or $R^a$ and $R^b$ together with the nitrogen to which they are attached form azetidinyl, pyrrolidinyl, or piperidinyl.

In another embodiment of the process of the invention, $R^1$ in ketoamide I and piperazine II is

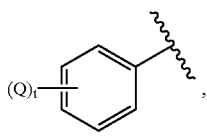

heterocycle, or substituted heterocycle;

wherein each Q is independently hydrogen, cyano, $C_1$–$C_4$ alkyl, or —O—$C_1$–$C_4$ alkyl; heterocycle is

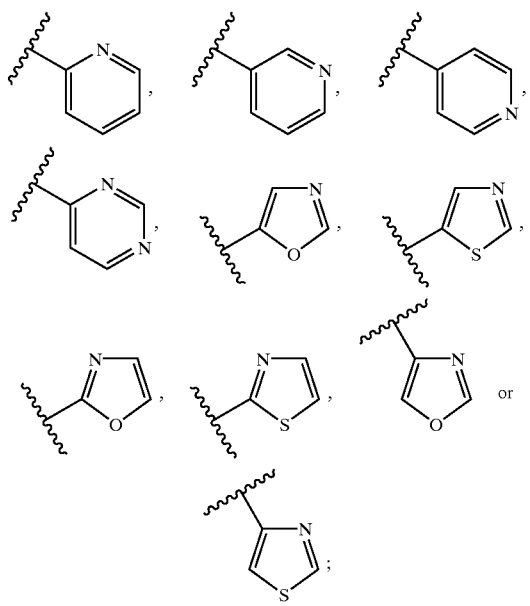

substituted heterocycle is heterocycle as defined above having from 1 to 3 substituents independently selected from $C_1$–$C_4$ alkyl, —O—$C_1$–$C_4$ alkyl, —S—$CH_3$, —N($CH_3$)$_2$, thiazolyl, and oxazolyl; and t is an integer equal to zero, 1 or 2.

In another embodiment, $R^1$ is:

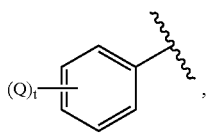

heterocycle, or substituted heterocycle;

wherein each Q is independently hydrogen, $C_1$–$C_4$ alkyl, or —O—$C_1$–$C_4$ alkyl;

heterocycle is

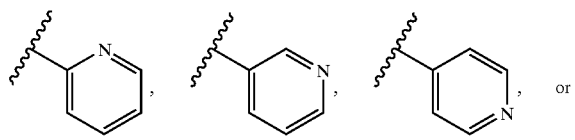

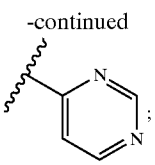

substituted heterocycle is heterocycle as defined above having from 1 to 3 substituents independently selected from $C_1$–$C_4$ alkyl, —O—$C_1$–$C_4$ alkyl, —S—$CH_3$, and —N($CH_3$)$_2$; and t is an integer equal to zero, 1 or 2.

In still another embodiment of the process, $R^1$ is pyridyl which is unsubstituted or substituted with 1 or 2 substituents independently selected from optionally substituted with $C_1$–$C_4$ alkyl or —O—$C_1$–$C_4$ alkyl. In an aspect of this embodiment, $R^1$ is pyridyl which is unsubstituted or substituted with methyl or methoxy. In another aspect of this embodiment, $R^1$ is:

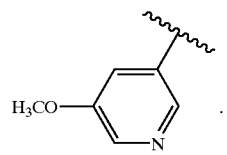

In an embodiment of the process of the invention, $R^2$ and $R^3$ in ketoamide I and piperazine II are each independently hydrogen or $C_1$–$C_4$ alkyl; or $R^2$ and $R^3$ together with the carbon to which they are attached form $C_1$–$C_6$ cycloalkyl. In another embodiment, $R^2$ and $R^3$ are either both —H or both methyl.

In an embodiment of the process of the invention, $R^6$ is as originally defined, except that each $R^c$ is —H. In other embodiments, $R^6$ is as originally defined, except that each $R^c$ is a —$C_1$–$C_4$ alkyl; or each $R^c$ is independently —H, methyl, or ethyl; or each $R^c$ is methyl.

In another embodiment, $R^6$ is $C_1$–$C_6$ alkyl optionally substituted with one or more halogens each of which is independently fluoro, chloro, or bromo. In another embodiment, $R^6$ is $C_1$–$C_4$ alkyl or $C_1$–$C_4$ fluoroalkyl. In still another embodiment, $R^6$ is

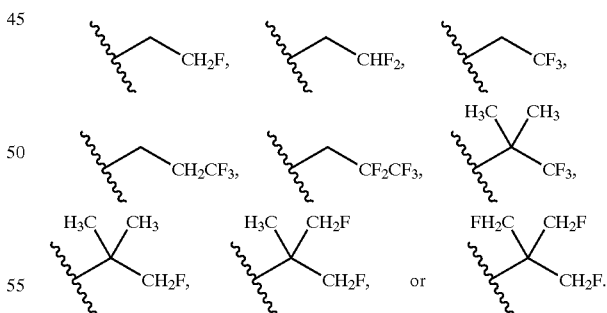

In an aspect of the preceding embodiment, $R^6$ is

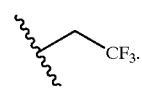

In the process of the invention, G is a nitrogen-protecting group. The choice of the nitrogen-protecting group is not critical. G can be, for example, any of the amino nitrogen protective groups described in T. W. Greene, *Protective Groups in Organic Synthesis*, John Wiley & Sons, 1981, pp. 218–287 and in T. W. Greene and P. G. M. Wuts, *Protective Groups in Organic Synthesis*, 2d edition, John Wiley & Sons, 1991, pp. 309–405. Suitable G groups include: (1) ($C_1$–$C_8$ alkyl)oxycarbonyl, (2) allyloxycarbonyl, (3) benzyloxycarbonyl wherein benzyl is optionally substituted with from 1 to 3 substituents each of which is independently halogen, $C_1$–$C_4$ alkyl or —O—$C_1$–$C_4$ alkyl, (4) p-nitrobenzyloxycarbonyl, (5) phenyloxycarbonyl wherein phenyl is optionally substituted with from 1 to 3 substituents each of which is independently $C_1$–$C_4$ alkyl or —O—$C_1$–$C_4$ alkyl, and (6) methylcarbonyl wherein the methyl is optionally substituted with from 1 to 3 substituents each of which is independently chloro or fluoro. In one embodiment, G is butyloxycarbonyl, t-amyloxycarbonyl, diisopropylmethyloxycarbonyl, allyloxycarbonyl, benzyloxycarbonyl, phenyloxycarbonyl, p-methoxybenzylcarbonyl, 2,4,6-trimethylbenzyloxycarbonyl, 3,5-dimethoxybenzyloxycarbonyl, p-nitrobenzyloxycarbonyl, 2,4-dichlorobenzyloxycarbonyl, or trifluoroacetyl. In an aspect of this embodiment, G is allyloxycarbonyl.

In the process of the invention, any amount of fuming sulfuric acid can be employed in Step A which results in the formation of at least some of Compound II. Of course, the maximum conversion of Compound I and maximum yield of Compound II is normally desired, and relative proportions of reactants and reagents suitable for this purpose are typically employed. In one embodiment, the fuming sulfuric acid (alternatively referred to herein as "oleum") is employed in an amount in the range of from about 5 to about 20 equivalents per equivalent of ketoamide I. In another embodiment, the fuming sulfuric acid is employed in an amount of from about 7 to about 11 equivalents per equivalent of ketoamide I. It is preferred to use the fuming sulfuric acid as the solvent for the reaction, although an inert co-solvent (e.g., an aliphatic hydrocarbon or an aromatic hydrocarbon) can be employed. Fuming sulfuric acid is commercially available in 15%, 20%, 30% and 60% grades. These grades can be used directly in Step A.

The oleum cyclization of ketoamide I in Step A is conducted in the presence of polyphosphoric acid. The cyclization of I with oleum alone can occur with significant racemization of stereocenter a, leading to a piperazine II product with lower optical purity. It has been found that the presence of polyphosphoric acid can significantly minimize racemization during oleum cyclization, resulting in a piperazine II with little or no degradation in optical purity. Polyphosphoric acid is suitably employed in Step A in an amount in the range of from about 0.5 to about 10 equivalents per equivalent of ketoamide I, and is typically employed in an amount of from about 2 to about 4 equivalents per equivalent of ketoamide I. In one embodiment, the ratio of equivalents of fuming sulfuric acid to equivalents of polyphosphoric acid is in the range from about 1:1 to about 30:1. In still another embodiment, the ratio of equivalents of fuming sulfuric acid to equivalents of polyphosphoric acid is in the range from about 2:1 to about 4:1. In still another embodiment, neat polyphosphoric acid is employed in Step A.

In an aspect of Step A, fuming sulfuric acid is employed in an amount in the range of from about 5 to about 20 equivalents and the polyphosphoric acid is employed in an amount in the range of from about 0.5 to about 10 equivalents per equivalent of ketoamide I. In another aspect, fuming sulfuric acid is employed in an amount in the range of from about 7 to about 11 equivalents and the polyphosphoric acid is employed in an amount in the range of from about 2 to about 4 equivalents per equivalent of ketoamide I.

Step A is suitably conducted at a temperature in the range of from about 0 to about 80° C. and is typically conducted at a temperature in the range of from about 25 to about 60° C. (e.g., from about 30 to about 50° C.).

In a suitable procedure for conducting Step A, liquid oleum is charged to the reaction vessel and cooled (e.g., to a temperature in the range of from about 5 to about 15° C.), after which polyphosphoric acid is slowly poured into the cooled oleum, followed by addition of ketoamide I while keeping the mixture cool (e.g., below about 25° C.). Upon completion of the ketoamide I addition, the mixture is heated to and maintained at a suitable reaction temperature until the reaction is complete or, alternatively, a desired amount of conversion is achieved. The reaction can be quenched by addition of water. The piperazine II can be recovered by conventional techniques, such as, for example, by adding an organic solvent to form an organic phase containing piperazine II and an aqueous phase, separating the phases, and recovering piperazine II from the organic phase (e.g., by concentrating and/or cooling the solution to precipitate piperazine II).

In still another aspect of Step A, the ketoamide I is employed as the sulfate salt (e.g., the bis-sulfate salt). The addition of the sulfate salt to the oleum has been found to be less exothermic than the addition of the corresponding free base. The use of the sulfate salt has also been found to avoid or minimize the formation of gummy solids that have been observed with the free base.

The ketoamide I reactant employed in Step A can be prepared, for example, by Scheme C as follows, wherein a, $R^1$, $R^2$, $R^3$, and $R^6$ are each as originally defined above with respect to process of the invention comprising Step A or as set forth in any of the foregoing embodiments or aspects of Step A:

SCHEME C:
Part 1:

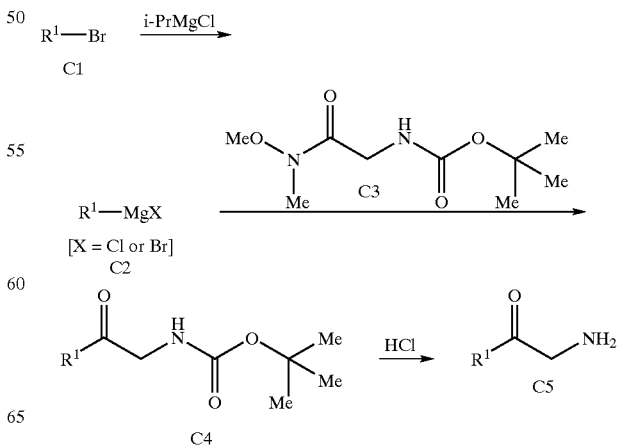

Part 2:

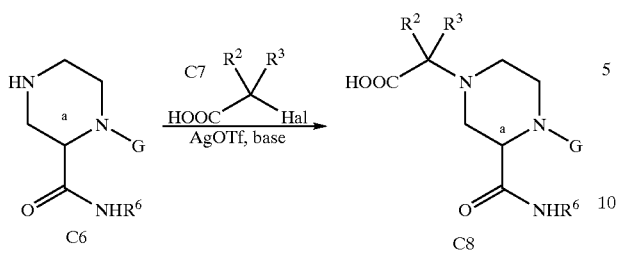

Part 3:

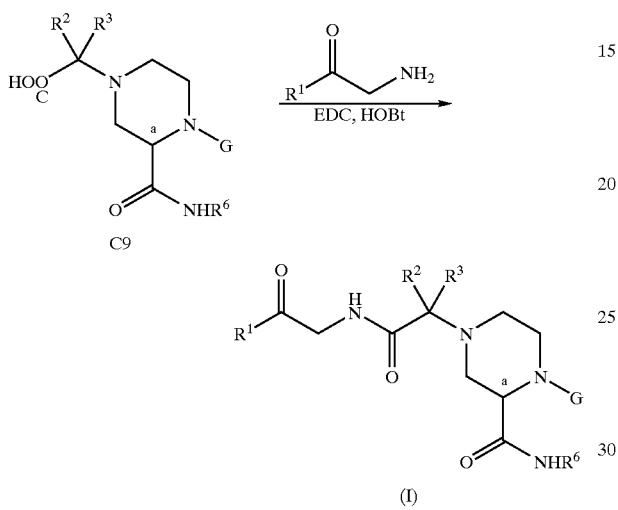

The present invention includes a process for preparing a Boc aminoketone of formula C4 which comprises:
  deprotonating Weinreb amide C3 by treatment with a Grignard of formula $(C_1-C_4$ alkyl)MgX wherein X is Cl or Br; and
  reacting the deprotonated Weinreb amide with Grignard C2 of formula $R^1$—MgX to obtain the Boc aminoketone C4.

In this process, $R^1$ in C2 and C4 is as originally defined above or as defined in any of the embodiments or aspects set forth for Step A. Both steps of this process are conducted in inert solvents such as dialkyl ethers (e.g., ethyl ether) and cyclic ethers and diethers (e.g., THF). In one embodiment, from about 0.9 to about 1.1 equivalents of $(C_1-C_4$ alkyl)MgX is employed per equivalent of C3 and from about 0.9 to about 1.1 equivalents of $R^1$—MgX is employed per equivalent of C3. The deprotonation step is typically conducted at a relatively low temperature; e.g., from about −10 to about 15° C. The reaction of the deprotonated Weinreb amide with $R^1$—MgX is typically conducted by adding $R^1$—MgX to the deprotonated Weinreb amide at a low temperature (e.g., from about −20 to about 0° C.), followed by warming the reaction mixture to a suitable reaction temperature (e.g., from about 20 to about 30° C.) and maintaining at reaction temperature until the reaction is complete. As an alternative to this process, the Weinreb amide C3 can be reacted directly with two equivalents of $R^1$—MgX to give C4. Deprotonation of the Weinreb amide prior to reaction with $R^1$—MgX can reduce costs, because the deprotonation can be achieved with one equivalent of a relatively inexpensive $(C_1-C_4$ alkyl)MgX such as isopropylMgCl, so that only one equivalent of the typically more expensive $R_1$—MgX is required to obtain C4. The process of the invention has also been found to result in a product C4 with improved purity compared to the product obtained by direct reaction of $R^1$—MgX with C3.

The present invention also includes a process for preparing Compound 16:

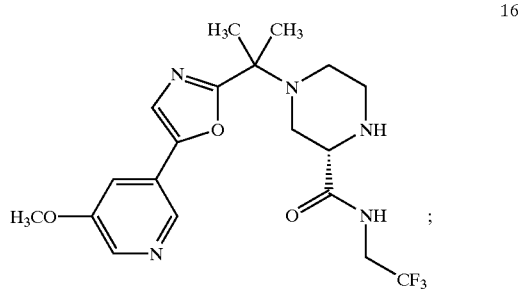

which comprises:
  (aa) treating ketoamide 15:

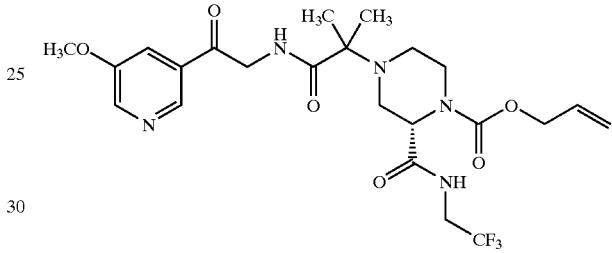

with fuming sulfuric acid in the presence of polyphosphoric acid to obtain Compound 16.

Embodiments of this process include the process as just described additionally incorporating one or more of the following features:
  the fuming sulfuric acid is employed in an amount in the range of from about 5 to about 20 equivalents (or from about 7 to about 11 equivalents) and the polyphosphoric acid is employed in an amount in the range of from about 0.5 to about 10 equivalents (of from about 2 to about 4 equivalents) per equivalent of ketoamide 15;
  the ratio of equivalents of fuming sulfuric acid to equivalents of polyphosphoric acid is in the range from about 1:1 to about 30:1 or from about 2:1 to about 4:1;
  the acid treatment of ketoamide 15 is conducted at a temperature in the range of from about 0 to about 80° C. or from about 25 to about 60° C. (e.g., from about 30 to about 50° C.); or
  the bis-sulfate salt of ketoamide 15 is employed in the process.

The present invention also includes a process for preparing a compound of Formula (IV):

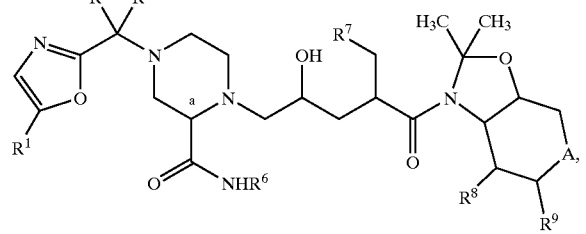

which comprises:
(A) treating a ketoamide of Formula (I):

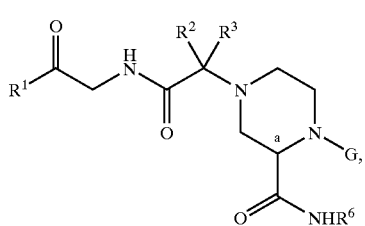
(I)

with fuming sulfuric acid in the presence of polyphosphoric acid to obtain a piperazine II:

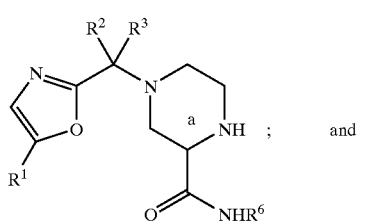
(II)

(B) reacting the piperazine II with an epoxide of Formula (III):

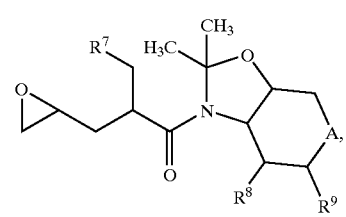
(III)

to obtain a compound of Formula (IV); wherein
stereocenter a, G, $R^1$, $R^2$, $R^3$, and $R^6$ are each as originally defined above in the discussion of Step A or as defined in any of the embodiments of Step A set forth above;
A is absent, $CH_2$, CHOH, O, or S;
$R^7$ is $C_1$-$C_6$ alkyl, $C_1$-$C_6$ cycloalkyl, aryl, or heteroaryl; wherein the alkyl or cycloalkyl is optionally substituted with one or more substituents (e.g., from 1 to 6, or from 1 to 5, or from 1 to 4, or from 1 to 3 substituents; or is di-substituted; or is mono-substituted) each of which is independently halogen, hydroxy, —$C_1$-$C_6$ haloalkyl, —O—$C_1$-$C_6$ alkyl, or —O—$C_1$-$C_6$ haloalkyl; and wherein aryl or heteroaryl is optionally substituted with one or more substituents (e.g., from 1 to 5, or from 1 to 4, or from 1 to 3 substituents; or is di-substituted; or is mono-substituted) each of which is independently halogen, hydroxy, —$C_1$-$C_6$ haloalkyl, —O—$C_1$-$C_6$ alkyl, —O—$C_1$-$C_6$ haloalkyl, $C_2$-$C_6$ alkenyl, or $C_2$-$C_6$ alkynyl; and
$R^8$ and $R^9$ are each independently —H, —$C_1$-$C_6$ alkyl, —$C_1$-$C_6$ haloalkyl, —$C_1$-$C_6$ cycloalkyl, or aryl, wherein the aryl is optionally substituted with one or more substituents (e.g., from 1 to 5, or from 1 to 4, or from 1 to 3 substituents; or is di-substituted; or is mono-substituted) each of which is independently halogen, —OH, —$C_1$-$C_6$ alkyl, —$C_1$-$C_6$ haloalkyl, —O—$C_1$-$C_6$ alkyl, or —O—$C_1$-$C_6$ haloalkyl; or alternatively $R^8$ and $R^9$ together with the carbons to which each is attached form a fused benzene ring which is optionally substituted with one or more substituents (e.g., from 1 to 4 or from 1 to 3 substituents; or is di-substituted; or is mono-substituted) each of which is independently halogen, —OH, —$C_1$-$C_6$ alkyl, —$C_1$-$C_6$ haloalkyl, —O—$C_1$-$C_6$ alkyl, or —O—$C_1$-$C_6$ haloalkyl.

Step A of this process has already been described in detail above. Step B involves the coupling of the epoxide III with the piperazine II with the opening of the epoxide ring to give Compound IV. It is to be understood that any embodiment or aspect of Step A set forth above can be employed with any embodiment or aspect of Step B as described below.

In an embodiment of the process, A in Compounds III and IV is absent, $CH_2$, or O.

In another embodiment of the process, $R^7$ in Compounds III and IV is $C_1$-$C_6$ alkyl, $C_1$-$C_6$ cycloalkyl, phenyl, substituted phenyl, heteroaryl, or substituted heteroaryl, wherein heteroaryl is selected from pyridyl, pyrazinyl, pyrimidinyl, thiophenyl, thiazolyl, pyridofuranyl, pyrimidofuranyl, pyridothienyl, pyridazothienyl, pyridooxazolyl, pyridazooxazolyl, pyrimidooxazolyl, pyridothiazolyl, and pyridazothiazolyl; and wherein substituted phenyl or substituted heteroaryl is substituted with one or more substituents (e.g., substituted with from 1 to 3 substituents, or substituted with 1 or 2 substituents), and each of the substituents on substituted phenyl or substituted heteroaryl is independently halogen, hydroxy, $C_1$-$C_6$ alkyl, $C_1$-$C_6$ fluoroalkyl, or —O—$C_1$-$C_6$ alkyl.

In another embodiment, $R^7$ in Compounds III and IV is

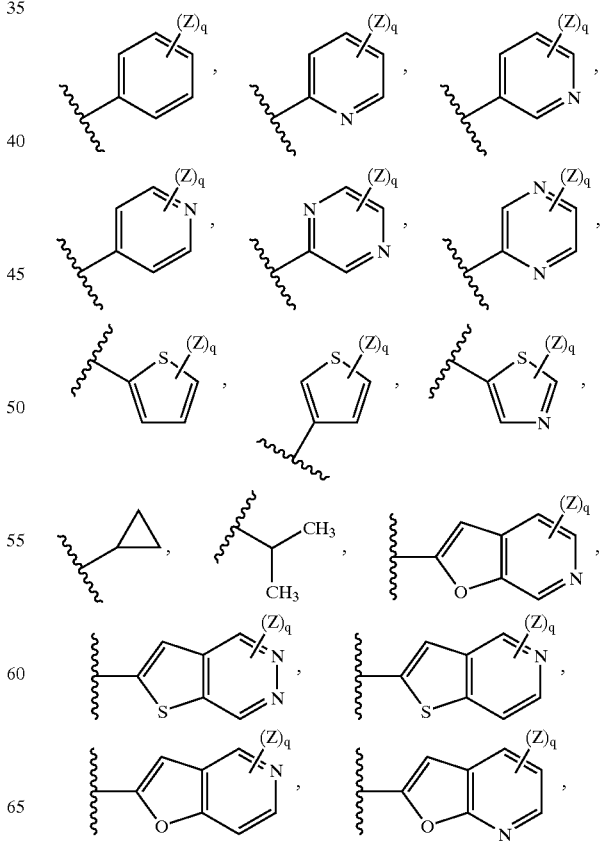

-continued

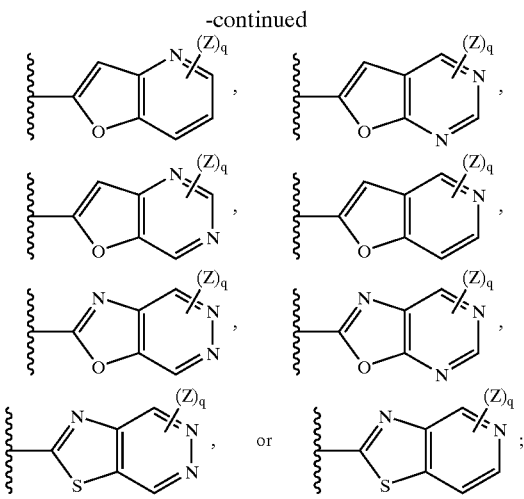

each Z is independently hydrogen, halogen, cyano, $C_1$–$C_6$ alkyl, or $C_1$–$C_6$ alkoxy; and q is an integer from 0 to 2.

In still another embodiment, $R^7$ in Compounds III and IV is

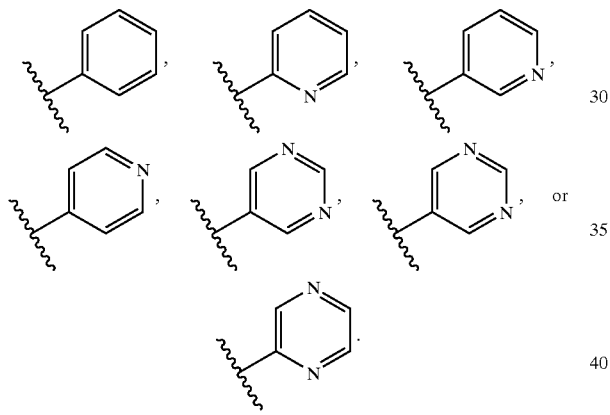

In still another embodiment, $R^7$ in Compounds III and IV is

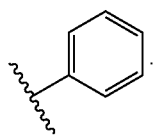

In another embodiment of the process, $R^8$ and $R^9$ are each independently —H, —$C_1$–$C_4$ alkyl, —$C_1$–$C_4$ fluoroalkyl, —$C_1$–$C_6$ cycloalkyl, or phenyl, wherein the phenyl is optionally substituted with one or more substituents (e.g., substituted with from 1 to 3 substituents, or substituted with 1 or 2 substituents) each of which is independently halogen, —$C_1$–$C_4$ alkyl, —$C_1$–$C_4$ fluoroalkyl, —O—$C_1$–$C_4$ alkyl, or —O—$C_1$–$C_4$ fluoroalkyl; or alternatively $R^8$ and $R^9$ together with the carbons to which each is attached form a fused benzene ring which is optionally substituted with one or more substituents (e.g., substituted with from 1 to 3 substituents, or substituted with 1 or 2 substituents) each of which is independently halogen, —$C_1$–$C_4$ alkyl, —$C_1$–$C_4$ fluoroalkyl, —O—$C_1$–$C_4$ alkyl, or —O—$C_1$–$C_4$ fluoroalkyl.

In another embodiment of the process, $R^8$ and $R^9$ are each independently —H, —$C_1$–$C_4$ alkyl, —$C_1$–$C_4$ fluoroalkyl, or phenyl; or alternatively $R^8$ and $R^9$ together with the carbons to which each is attached form a fused benzene ring which is optionally substituted with one or more substituents (e.g., substituted with from 1 to 3 substituents, or substituted with 1 or 2 substituents) each of which is independently halogen, —$C_1$–$C_4$ alkyl, —$C_1$–$C_4$ fluoroalkyl, —O—$C_1$–$C_4$ alkyl, or —O—$C_1$–$C_4$ fluoroalkyl.

In another embodiment of the process, Compound III (and the corresponding moiety in Compound IV) is:

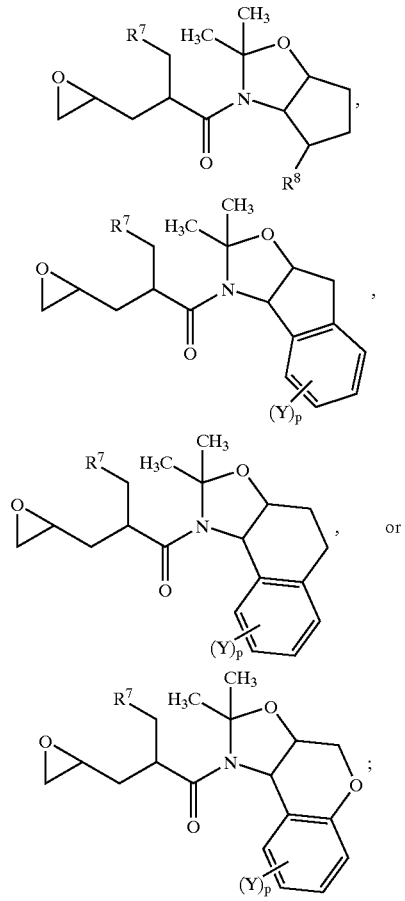

wherein $R^7$ and $R^8$ are each as originally defined or as defined in any of the preceding embodiments; each Y is independently —H, halogen, —$C_1$–$C_4$ alkyl, —$C_1$–$C_4$ fluoroalkyl, or —O—$C_1$–$C_4$ alkyl; and p is an integer equal to zero, 1 or 2.

In still another embodiment of the process, Compound III is:

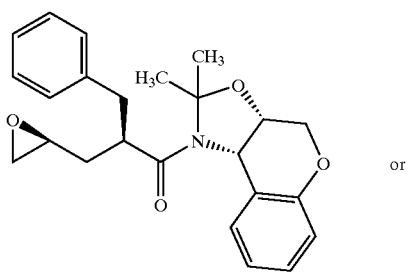

-continued

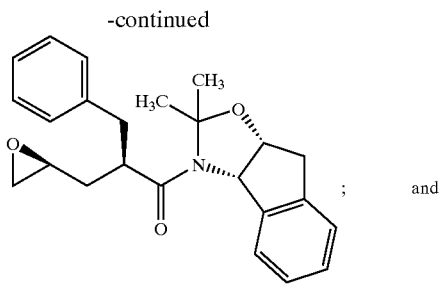
; and the corresponding moiety in Compound IV is:

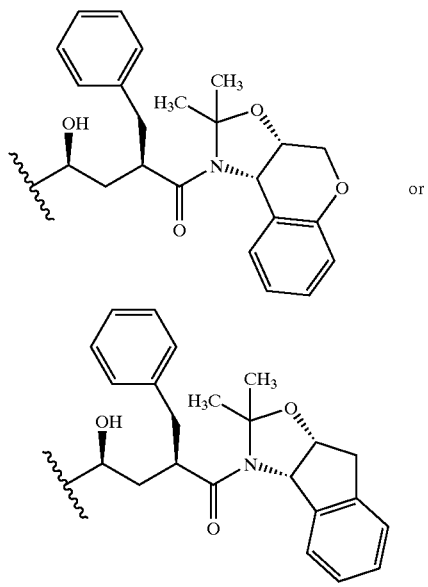

respectively.

Step B is suitably conducted in a solvent. The solvent employed in the coupling reaction can be any organic compound which under the reaction conditions employed is in the liquid phase, is chemically inert, and will dissolve, suspend, and/or disperse the reactants. Suitable solvents include hydrocarbons, ethers, alcohols, nitrites, and esters. In one embodiment, the solvent is selected from the group consisting of $C_3$–$C_{10}$ linear and branched alkanes, $C_1$–$C_{10}$ linear and branched halogenated alkanes, $C_5$–$C_{10}$ cycloalkanes, $C_6$–$C_{14}$ aromatic hydrocarbons, dialkyl ethers wherein each alkyl is independently a $C_1$–$C_6$ alkyl, $C_1$–$C_6$ linear and branched alkanes substituted with two —O—$C_1$–$C_6$ alkyl groups (which are the same or different), $C_4$–$C_8$ cyclic ethers and diethers, $C_6$–$C_8$ aromatic ethers, $C_1$–$C_6$ alkyl esters of $C_1$–$C_6$ alkylcarboxylic acids, $C_1$–$C_{10}$ alkyl alcohols, $C_2$–$C_6$ aliphatic nitriles, and $C_7$–$C_{10}$ aromatic nitriles. Exemplary solvents include carbon tetrachloride, chloroform, methylene chloride, 1,2-dichloroethane (DCE), 1,1,2-trichloroethane (TCE), 1,1,2,2-tetrachloroethane, cyclohexane, toluene, o- and m- and p-xylene, ethylbenzene, ethyl ether, MTBE, THF, dioxane, 1,2-dimethoxyethane (DME), anisole, phenetole, methyl acetate, ethyl acetate, ethanol, n- and iso-propanol, tert-butyl alcohol, tert-amyl alcohol, acetonitrile, propionitrile, benzonitrile, and p-tolunitrile.

In another embodiment, the solvent employed in Step B is a $C_1$–$C_6$ alkyl alcohol. In an aspect of this embodiment, the alcohol is methanol, ethanol, isopropanol, t-butyl alcohol, or t-amyl alcohol.

Step B is suitably conducted at a temperature in the range of from about room temperature up to the reflux temperature of the chosen solvent. In one embodiment, the reaction is conducted at a temperature in the range of from about 20 to about 100° C. In other embodiments, the temperature is in the range of from about 30 to about 95° C., or is in the range of from about 40 to about 95° C. (e.g., from about 45 to about 65° C.).

Piperazine II and epoxide III can be employed in any proportion which will result in the formation of at least some of Compound IV. Typically, however, the reactants are employed in proportions which will optimize conversion of at least one of the reactants. In one embodiment, the amount of piperazine II employed in Step B is at least about 0.5 equivalent per equivalent of epoxide III, and is typically in the range of from about 1 to about 5 (e.g., from about 1 to about 3) equivalents per equivalent of epoxide III. In another embodiment, piperazine II is employed in an amount of from about 1 to about 2 (e.g., from about 1 to about 1.5) equivalents per equivalent of epoxide III. In an aspect of the preceding embodiment, piperazine II is employed in an amount of from about 1 to about 1.1 equivalents per equivalent of epoxide III.

The solvent, piperazine II, and epoxide III can be charged to the Step B reaction vessel concurrently or sequentially in any order. In a suitable procedure, the piperazine II is dissolved in the chosen solvent, followed by addition of epoxide III. The mixture is then stirred at a suitable reaction temperature until the reaction is complete or, alternatively, until the desired or optimum degree of conversion is obtained.

Product IV can be recovered via conventional techniques, such as by treating a solution of IV with silica gel and/or activated carbon to remove impurities, filtering the solution, concentrating and cooling the filtrate to precipitate IV and separating IV by filtration.

Epoxides of Formula (III) for use in Step B can be prepared via the methods (or routine modifications thereof) described in U.S. Pat. No. 5,728,840.

The present invention also includes a process which comprises Steps A and B as heretofore described, and which further comprises:

(C) treating Compound IV with acid to obtain a compound of Formula (V):

(V)

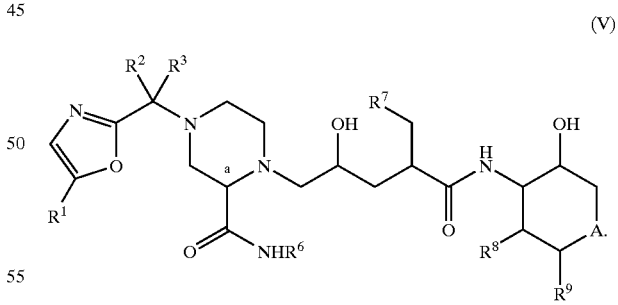

Step C is an acid deprotection step which affords Compound V, wherein stereocenter a, A, $R^1$, $R^2$, $R^3$, $R^6$, $R^7$, $R^8$, and $R^9$ are as originally defined above in the discussion of Steps A and B or as defined in any of the embodiments of Steps A and B as set forth above. Compounds of Formula (V) are inhibitors of HIV protease, and certain classes of the compounds encompassed by Formula (V) (e.g., those in which $R^6$=fluoroalkyl such as 2,2,2-trifluoroethyl) are inhibitors of mutant forms of HIV protease which are resistant to conventional protease inhibitors such as indinavir. Compounds representative of the classes of compounds of Formula (V) capable of inhibiting mutant protease have exhibited $IC_{50}$ values below 1 nM against the wild-type enzyme and below 5 nM against the mutant enzymes Q-60, K-60, and V-18 in the assay for inhibition of microbial expressed HIV protease described in International Publication No. WO 01/05230. These compounds have also exhibited $CIC_{95}$ values below 50 nM against the wild-type viral construct and $CIC_{95}$ values below 125 nM against the viral constructs Q60, K-60, and V-18 in the cell spread assay described in WO 01/05230. These compounds are generally much more potent in both of these assays than indinavir. Further description of these compounds can be found in WO 01/38332.

In Step C, Compound IV is dissolved in a suitable solvent and brought into contact with the acid. Suitable solvents include polar organic solvents which are chemically inert under the conditions employed in Step C, such as alcohols and ethers. In one embodiment, the solvent is a dialkyl ether wherein each alkyl is independently a $C_1$–$C_6$ alkyl, $C_1$–$C_6$ linear or branched alkane substituted with two —O—$C_1$–$C_6$ alkyls (which are the same or different), a $C_4$–$C_8$ cyclic ether and diether, or a $C_1$–$C_6$ alkyl alcohol. In an aspect of this embodiment, the solvent is a $C_1$–$C_6$ alkyl alcohol (e.g., methanol).

The acid is suitably a strong acid such as trifluoroacetic acid or HCl. The acid can be introduced directly into a solution of Compound IV (e.g., bubbling gaseous HCl into the solution) or can be charged in the form of a solution, such as an aqueous solution or a solution in suitable organic solvent such as an alcohol (e.g., methanol) or an ether (e.g., THF). The acid treatment is generally conducted at a relatively low temperature (e.g., suitably less than about 20° C. and more suitably less than about 10° C.). Typically at least about 1 equivalent of acid is employed in Step C per equivalent of Compound IV, and an excess amount of the acid is typically employed. In a suitable procedure, a solution of the acid is added slowly (e.g., dropwise) to a solution of Compound IV while maintaining the solution at a relatively low temperature, in order to avoid a rapid accumulation of heat. Once the reaction is complete or the desired degree of conversion has been obtained, the reaction mixture can be quenched with base and product V recovered by conventional means.

The present invention also includes a process for preparing Compound 25:

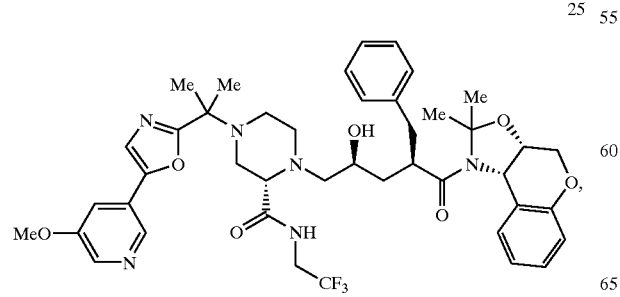

which comprises:
(aa) treating ketoamide 15:

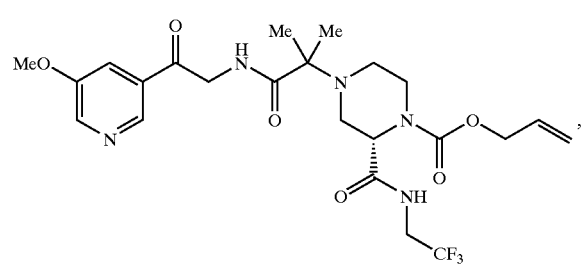

with fuming sulfuric acid in the presence of polyphosphoric acid to obtain piperazine 16:

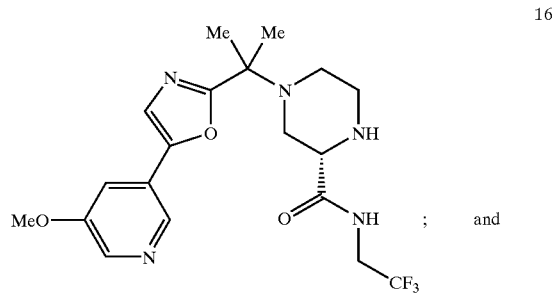
; and (bb) reacting piperazine 16 with epoxide 24:

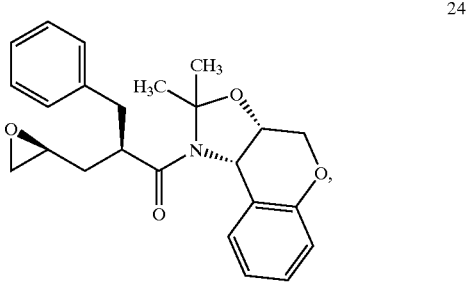

to obtain compound 25.

Embodiments of this process include the process as just described incorporating one or more of the following features:

the fuming sulfuric acid is employed in Step (aa) in an amount in the range of from about 5 to about 20 equivalents (or from about 7 to about 11 equivalents) and the polyphosphoric acid is employed in an amount in the range of from about 0.5 to about 10 equivalents (of from about 2 to about 4 equivalents) per equivalent of ketoamide 15;

the ratio of equivalents of fuming sulfuric acid to equivalents of polyphosphoric acid in Step (aa) is in the range from about 1:1 to about 30:1 or from about 2:1 to about 4:1;

the acid treatment of ketoamide 15 is conducted at a temperature in the range of from about 0 to about 80° C. or from about 25 to about 60° C. (e.g., from about 30 to about 50° C.);

the bis-sulfate salt of ketoamide 15 is employed in Step (aa);

Step (bb) is conducted in a solvent selected from the group consisting of dialkyl ethers wherein each alkyl is independently a $C_1$–$C_6$ alkyl, $C_1$–$C_6$ linear and branched alkanes substituted with two —O—$C_1$–$C_6$ alkyl groups (which are the same or different), $C_4$–$C_8$ cyclic ethers and diethers, $C_6$–$C_8$ aromatic ethers, $C_1$–$C_6$ alkyl esters of $C_1$–$C_6$ alkylcarboxylic acids, $C_1$–$C_{10}$ alkyl alcohols, $C_2$–$C_6$ aliphatic nitriles, and $C_7$–$C_{10}$ aromatic nitriles;

Step (bb) is conducted in a solvent which is a $C_1$–$C_6$ alkyl alcohol;

in Step (bb) piperazine 16 is employed in an amount in the range of from about 1 to about 3 equivalents (e.g., from about 1 to about 1.5 equivalents) per equivalent of Compound 24; or the reaction in Step (bb) is conducted at a temperature in the range of from about 40 to about 95° C. (e.g., from about 45 to about 65° C.).

The present invention further includes a process for preparing Compound 26:

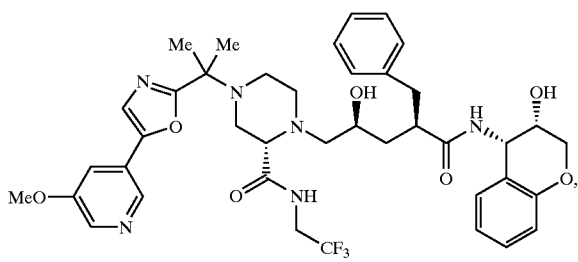

26 which comprises Steps (aa) and (bb) as set forth above and further comprises:

(cc) treating Compound 25 with acid to obtain Compound 26.

Embodiments of this process include the process as just described incorporating one or more of the following features:

the acid in Step (cc) is an aqueous solution of HCl;

the acid in Step (cc) is a solution of HCl in a $C_1$–$C_6$ alkyl alcohol (e.g., ethanol);

Step (cc) is conducted at a temperature of less than about 10° C. (e.g., in the range of from about −10 to about 10° C.); or the acid is employed in an amount of at least about 1 equivalent per equivalent of Compound 25.

Other embodiments of the present invention include the process for preparing Compound 26 via Steps (aa), (bb) and (cc), as originally defined above, additionally incorporating any one or more of the embodiments set forth above for any one or more of Steps (aa), (bb), and (cc).

The present invention also includes a process for enhancing the optical purity of a piperazine of Formula (II):

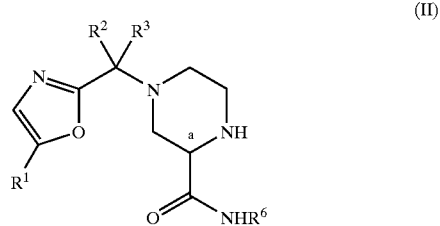

(II)

which comprises:

(X) forming a solution comprising piperazine II containing a minor portion of undesired optical isomer, 2-naphthalenesulfonic acid, and solvent; and (Y) crystallizing from the solution a crystalline 2-naphthalenesulfonic acid salt of II having enhanced optical purity;

wherein stereocenter a, $R^1$, $R^2$, $R^3$ and $R^6$ are each as originally defined above in Step A or as defined in any embodiments of Step A set forth above.

A "minor portion" in Step X means that undesired optical isomer is present in an amount less than the desired optical isomer. Typically undesired optical isomer is present in an amount of no more than about 15 wt. %, and more typically is present in an amount of less than about 10 wt. %, or even less than about 5 wt. %. Undesired optical isomer includes any isomer(s) of piperazine II which have the undesired configuration at stereocenter a. For example, if the optical purity of piperazine II with stereocenter a in the S configuration is to be enhanced, then the undesired material includes isomer(s) of piperazine II having stereocenter a in the R configuration, irrespective of the occurrence of other chiral centers in the isomer.

The term "enhanced optical purity" means that the crystallized 2-naphthalenesulfonic acid (alternatively referred to herein as "2-NSA") salt of II contains a greater proportion of the desired configuration at stereocenter a than the piperazine II starting material.

In an embodiment of this process, $R^1$ in piperaine II is pyridyl which is unsubstituted or substituted with 1 or 2 substituents each of which is independently $C_1$–$C_4$ alkyl or —O—$C_1$–$C_4$ alkyl; $R^2$ and $R^3$ are either both —H or both methyl; and $R^6$ is $C_1$–$C_4$ alkyl or $C_1$–$C_4$ fluoroalkyl.

The solvent employed in the process can be any organic substance which is chemically inert under the conditions employed in Step X and Step Y and which can dissolve piperazine II and optical isomers thereof and 2-NSA. A suitable class of solvents is the nitriles, including the $C_2$–$C_6$ aliphatic nitriles. A preferred solvent is acetonitrile. In one embodiment, water is employed as a co-solvent with the nitrile solvent. Water co-solvent has been found to promote formation of the solution in Step X. In an aspect of the preceding embodiment, the solvent is acetonitrile and the volume ratio of acetonitrile to water employed in Step X is suitably in the range of from about 1.5:1 to about 10:1, and is typically in the range of from about 2:1 to about 5:1.

In another embodiment of the process, the solvent is acetonitrile and the piperazine II is suitably employed in Step X in an amount in the range of from about 0.01 to about 0.2 grams per mL of acetonitrile, is typically employed in an amount in the range of from about 0.02 to 0.1 g/mL, and is often employed in an amount in the range of from about 0.05 to about 0.07 g/mL.

The 2-NSA can be employed in the process in any proportion with respect to piperazine II which will lead to the formation of a crystalline salt having enhanced optical purity. In one embodiment, the 2-NSA is employed in Step X in an amount in the range of from about 2.5 to about 3.5 equivalents per equivalent of II. In another embodiment, 2-NSA is employed in an amount in the range of from about 2.8 to about 3.0 equivalents per equivalent of II.

In an embodiment of the process, forming the solution in Step X comprises heating a mixture comprising piperazine II containing a minor portion of undesired optical isomer, 2-naphthalenesulfonic acid, and solvent to a temperature sufficient to effect dissolution. In an aspect of this embodiment, the solvent is a nitrile (e.g., acetonitrile), water is employed as a co-solvent, and the mixture is heated to a temperature in the range of from about 30 to about 100° C. (e.g., from about 40 to about 80° C. or from about 50 to about 60° C.). (It is noted that if the reflux temperature of the mixture is below the desired or required dissolution temperature, then a higher than ambient pressure can be applied to achieve the desired temperature.)

Crystallizing the 2-NSA salt of piperazine II in Step Y can be accomplished by cooling, or by concentrating (e.g., by evaporative removal of solvent using heat and/or vacuum), or by both cooling and concentrating (concurrently or sequentially in either order) the solution resulting from Step X. In one embodiment, crystallizing Step Y comprises seeding the solution of Step X with crystalline 2-naphthalenesulfonate salt of II, aging the seeded solution, and then either (i) cooling or concentrating or (ii) cooling and concentrating (concurrently or sequentially in either order) the solution to obtain the crystalline 2-naphthalenesulfonic acid salt of II having enhanced optical purity.

As used herein with respect to a crystallization process, the term "aging" and variants thereof (e.g., "aged") mean allowing the components of the solution (e.g., 2-NSA, piperazine H, and the crystal salt thereof) to stay in contact for a time and under conditions effective for completion or optimization of the crystallization. The term "aging" and its variants can also refer herein to allowing the reactants of a given reaction to stay in contact for a time and under conditions effective for completion of the reaction. The proper meaning of "aging" is clear from the context in which it is used.

Another embodiment of the process comprising Steps X and Y as originally defined above is the process wherein piperazine II is a piperazine of Formula (II'):

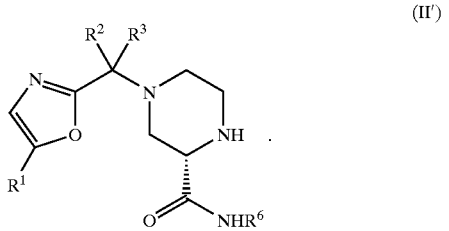

(II')

Any one or more of the embodiments of the process set forth above for piperazine II can be incorporated into this embodiment, and each such incorporation represents an additional aspect of this embodiment.

The present invention further includes a process which comprises Step A as originally defined and described above, which further comprises:

(X) forming a solution comprising the piperazine II product of Step A containing a minor portion of undesired optical isomer, 2-naphthalenesulfonic acid, and solvent; and (Y) crystallizing from the solution a crystalline 2-naphthalenesulfonic acid salt of II having enhanced optical purity.

Embodiments of this process include the process as just defined incorporating one or more of the embodiments, aspects or features of any one or more of Steps A, X and Y as heretofore described.

The present invention also includes a process for preparing Compound IV which comprises Steps A and B as set forth above and further comprises:

(X) forming a solution comprising the piperazine II product of Step A containing a minor portion of undesired optical isomer, 2-naphthalenesulfonic acid, and solvent; and (Y) crystallizing from the solution a crystalline 2-naphthalenesulfonic acid salt of II having enhanced optical purity; and (Z) treating the crystallized salt of II with base (e.g., NaOH) to break the salt and afford Compound II as free base for use in Step B.

Additional embodiments of this process include the process as just described additionally incorporating one or more of the embodiments, aspects, or features of any one or more of Steps A, B, X and Y as defined and described above.

The present invention also includes a process for enhancing the optical purity of Compound 16:

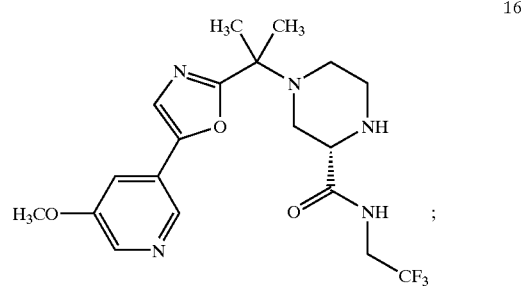

16 which comprises:

(xx) forming a solution comprising Compound 16 containing a minor portion of its optical isomer, 2-naphthalenesulfonic acid, acetonitrile, and water;

(yy) crystallizing from the solution a crystalline tris-2-naphthalenesulfonate salt of 16 having enhanced optical purity.

In an embodiment of this process, forming the solution in Step (xx) comprises heating a mixture comprising Compound 16 containing a minor portion of its optical isomer, 2-naphthalenesulfonic acid, acetonitrile, and water to a temperature sufficient to effect dissolution; and crystallizing Step (yy) comprises (i) cooling or concentrating or (ii) cooling and concentrating (concurrently or sequentially in either order) the solution to obtain crystalline tris-2-naphthalenesulfonate salt of 16 with enhanced optical purity. In an aspect of the preceding embodiment, Step (yy) comprises seeding the heated solution of Step (xx) with crystalline tris-naphthalene sulfonate salt of 16, aging the seeded solution at elevated temperature (e.g., a temperature in the range of from about 40 to about 80° C.), and then either (i) cooling or concentrating or (ii) cooling and concentrating (concurrently or sequentially in either order) the solution to obtain crystalline tris-2-naphthalenesulfonate salt of 16 with enhanced optical purity.

Additional embodiments of this process include the process as originally described or as described in the preceding embodiment incorporating one or more of the following features:

the volume ratio of acetonitrile to water employed in Step (xx) is in the range of from about 1.5:1 to about 10:1, or from about 2:1 to about 5:1;

Compound 16 is employed in Step (xx) in an amount in the range of from about 0.01 to about 0.2 grams per mL of acetonitrile, or from about 0.05 to about 0.07 g/mL of acetonitrile;

2-naphthalenesulfonic acid is employed in Step (xx) in an amount in the range of from about 2.5 to about 3.5 equivalents per equivalent of 16, or from about 2.8 to about 3.0 equivalents per equivalent of 16; or the solution in Step (xx) is formed by heating the mixture to a temperature in the range of from about 30 to about 100° C., or from about 40 to about 80° C., or from about 50 to about 60° C.

The present invention also includes a process which comprises Step (aa) as originally defined and described above, which further comprises:

(xx) forming a solution comprising the Compound 16 product of Step (aa) containing a minor portion of its optical isomer, 2-naphthalenesulfonic acid, acetonitrile, and water;

(yy) crystallizing from the solution a crystalline tris-2-naphthalenesulfonate salt of 16 having enhanced optical purity.

Embodiments of this process include the process as just defined incorporating one or more of the embodiments, aspects or features of any one or more of Steps (aa), (xx) and (yy) as heretofore described.

The present invention also includes a 2-naphthalenesulfonic acid salt of a piperazine of Formula IIa or IIb:

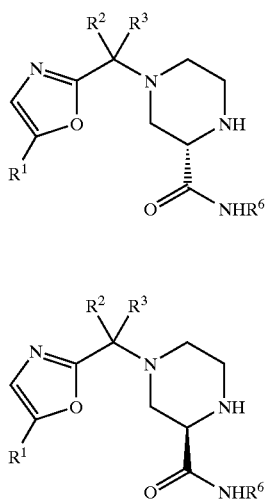

wherein $R^1$, $R^2$, $R^3$, and $R^6$ are each as originally defined above in Step A or as defined in any of the embodiments, aspects or features of Step A as set forth above.

In one embodiment, the salt is a salt of a piperazine of Formula (IIa), wherein $R^1$ is pyridyl which is unsubstituted or substituted with 1 or 2 substituents independently selected from optionally substituted with $C_1$–$C_4$ alkyl or —O—$C_1$–$C_4$ alkyl;

$R^2$ and $R^3$ are either both —H or both methyl; and $R^6$ is $C_1$–$C_4$ alkyl or $C_1$–$C_4$ fluoroalkyl.

In an aspect of the foregoing embodiment, the salt is a tris-(2-naphthalenesulfonic acid) salt of the piperazine of Formula (IIa). In another aspect of the foregoing embodiment, the salt is a tris-(2-naphthalenesulfonic acid) salt of Compound 16:

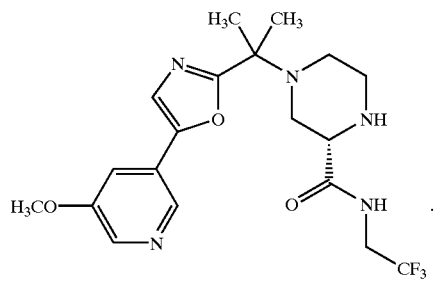

The present invention also includes a process for preparing Compound 25 which comprises Steps (aa) and (bb) as set forth above and further comprises:

(xx) forming a solution comprising Compound 16 as obtained from Step (aa) and containing a minor portion of its optical isomer, 2-naphthalenesulfonic acid, acetonitrile, and water;

(yy) crystallizing from the solution a crystalline tris-2-naphthalenesulfonate salt of 16 having enhanced optical purity; and (zz) treating the crystallized salt of 16 with base (e.g., NaOH) to break the salt and afford Compound 16 as free base for use in Step (bb).

Additional embodiments of this process include the process as just described additionally incorporating one or more of the embodiments, aspects, or features of any one or more of Steps (aa), (bb), (xx), or (yy) as defined and described above.

The present invention also includes a process for purifying 2-naphthalenesulfonic acid, which comprises (L) heating a mixture comprising crude 2-naphthalenesulfonic acid, acetonitrile, and toluene to a temperature sufficient to dissolve the crude acid and form a system comprising an upper layer containing the major portion of 2-naphthalenesulfonic acid and a lower layer;

(M) separating the upper layer from the lower layer; and (N) crystallizing purified 2-naphthalenesulfonic acid from the separated upper layer.

The term "crude 2-naphthalenesulfonic acid" refers to 2-NSA which comprises in addition to 2-NSA per se at least one of 1-NSA, sulfuric acid, a naphthalene sulfone, or naphthalene. These impurity components suitably represent a minor amount (i.e., a total of less than 50 wt. %) of the crude 2-NSA, and typically represent less than about 35 wt. % of the crude 2-NSA. Relatively pure 2-NSA (not commercially available) is preferred for use in the processes described above for enhancing the optical purity of piperazine II and piperazine 16. The process comprising Steps L, M and N can provide 2-NSA with a suitable level of purity.

The volume ratio of acetonitrile to toluene in Step L is suitably in the range of from about 1:1 to about 1:8, is typically in the range of from about 1:2 to about 1:6, and is more typically in the range of from about 1:2 to about 1:4.

The amount of crude 2-naphthalenesufonic acid can vary from an amount providing a very dilute to an amount providing a highly concentrated solution. In one embodiment, the crude 2-NSA is suitably present in Step L in an amount in the range of from about 0.1 to about 1 g per mL of acetonitrile. In another embodiment, crude 2-NSA is present in Step L in an amount in the range of from about 0.2 to about 0.8 g per mL of acetonitrile. In still another embodiment, crude 2-NSA is present in an amount in the range of from about 0.4 to about 0.6 g per mL of acetonitrile.

The temperature required in Step L to dissolve the crude acid depends upon the relative proportion of the solvent (acetonitrile and toluene) employed, higher temperatures being required to form a highly concentrated solution. The temperature is suitably in the range of from about 40 to about 100° C., and is typically in the range of from about 50 to about 90° C. (e.g., from about 70 to about 90° C.).

Water can be added to the mixture of Step L in order to promote separation of the layers. Typically no more than about 5 wt. % of water with respect to crude 2-NSA is employed for this purpose, and more typically no more than about 2.5 wt. %

Crystallization in Step N can be achieved by conventional methods such as cooling the solution, or concentrating the solution (e.g., by evaporative removal of solvent using heat and/or vacuum), or cooling and concentrating (concurrently or sequentially in either order) the solution. In one embodiment, crystallizing in Step N comprises seeding the cooled and/or concentrated upper layer with 2-naphthalenesulfonic acid crystals to obtain purified crystalline 2-naphthalenesulfonic acid.

In another embodiment, crystallizing in Step N comprises adding a minor portion of water to the hot top layer, and then (i) cooling or concentrating or (ii) cooling and concentrating (concurrently or sequentially in either order) the layer to form purified crystals of 2-NSA. The amount of water added to the hot top layer is suitably no more than about 10 wt. %, and typically is no more than about 5 wt. % (e.g., from about 1 to about 5 wt. %) of the crude 2-NSA.

In still another embodiment, crystallizing in Step N comprises adding water to the hot top layer and cooling the layer to form an organic upper phase and an aqueous lower phase containing the major portion of 2-naphthalenesulfonic acid, separating and solvent switching the aqueous phase with acetonitrile, adding toluene and heating to form a clear solution, and then (i) cooling or concentrating or (ii) cooling and concentrating (concurrently or sequentially in either order) the switched solution to form purified crystals of 2-naphthalenesulfonic acid. The amount of water added to the hot top layer is suitably at least about 50 wt. %, and typically is at least about 75 wt. % (e.g., from about 75 to about 95 wt. %) of the crude 2-NSA.

If desired, further purification of the crystallized 2-NSA can be achieved by recrystallization of the isolated Step N crystals from acetonitrile.

Still other embodiments of the present invention include any of the processes as originally defined and described above and any embodiments or aspects thereof as heretofore defined, further comprising isolating (which may be alternatively referred to as recovering) the compound of interest from the reaction or crystallization medium (e.g., Compound IV or Compound 25, or piperazine II or piperazine 16).

If desired, the progress of the reaction in any of the above-described chemical reactions can be followed by monitoring the disappearance of a reactant (e.g., piperazine I or epoxide III in Step B) and/or the appearance of the product (e.g., Compound IV in Step B) using TLC, HPLC, NMR or GC.

As used herein, the term "$C_1$–$C_6$ alkyl" means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl.

The term "—O—$C_1$–$C_6$ alkyl" refers to an alkoxy group wherein the alkyl is $C_1$ to $C_6$ alkyl as defined above. "—O—$C_1$–$C_4$ alkyl" has an analogous meaning; i.e., it is an alkoxy group selected from methoxy, ethoxy, n-propoxy, isopropoxy, n-butoxy, isobutoxy, tert-butoxy, and sec-butoxy.

The term "halogen" (which may alternatively be referred to as "halo") refers to fluorine, chlorine, bromine and iodine (alternatively, fluoro, chloro, bromo, and iodo).

The term "$C_1$–$C_6$ haloalkyl" means a $C_1$ to $C_6$ linear or branched alkyl group as defined above with one or more halogen substituents. The term "$C_1$–$C_4$ haloalkyl" has an analogous meaning.

The term "—O—$C_1$–$C_6$ haloalkyl" means an alkoxy group as defined above with one or more halogen substituents on the alkyl moiety. The term "—O—$C_1$–$C_4$ haloalkyl" has an analogous meaning.

The term "$C_1$–$C_6$ fluoroalkyl" means a $C_1$–$C_6$ alkyl group as defined above with one or more fluorine substituents. The term "$C_1$–$C_4$ fluoroalkyl" has an analogous meaning. Representative examples of suitable fluoroalkyls include the series $(CH_2)_{0-3}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl:

The term "—O—$C_1$–$C_6$ fluoroalkyl" means an —O—$C_1$–$C_6$ alkyl group as defined above wherein the alkyl moiety has one or more fluorine substituents. The term "—O—$C_1$–$C_4$ fluoroalkyl" has an analogous meaning. Representative examples include the series $O(CH_2)_{0-3}CF_3$ (i.e., trifluoromethoxy, 2,2,2-trifluoroethoxy, 3,3,3-trifluoro-n-propoxy, etc.), and 1,1,1,3,3,3-hexafluoroisopropoxy.

The term "$C_3$–$C_8$ cycloalkyl" refers to a cyclic ring selected from cyclopropyl, cyclobutyl, cyclopentyl, cyclohexyl, cycloheptyl, and cyclooctyl. "$C_1$–$C_6$ cycloalkyl" has an analogous meaning.

The term "$C_3$–$C_6$ azacycloalkyl" refers to a saturated cyclic ring containing a ring nitrogen and from 3 to 6 ring carbons. The term includes azetidinyl, pyrrolidinyl, piperidinyl, and hexahydroazepinyl.

The term "aryl" refers herein to phenyl or naphthyl.

The term "heteroaryl" refers to (i) a 5- or 6-membered aromatic ring consisting of carbon atoms and from 1 to 3 heteroatoms selected from N, S, and O or (ii) an 8- to 10-membered bicyclic ring system consisting of carbon atoms and from 1 to 3 heteroatoms selected from N, S, and O, wherein at least one of the rings in the bicyclic system is an aromatic ring. The heteroaryl ring may be attached at any heteroatom or carbon atom, provided that attachment results in the creation of a stable structure.

The term "substituted" (e.g., as in "substituted heterocycle") includes mono- and poly-substitution by a named substituent or substituents to the extent such single and multiple substitution (including multiple substitution at the same site) is chemically allowed.

The symbol "∼∼∼" in front of an open bond in the structural formula of a group marks the point of attachment of the group to the rest of the molecule.

Combinations of substituents and/or variables are permitted only to the extent such combinations result in chemically stable compounds under the process conditions described herein.

Abbreviations used herein include the following:
ACN=acetonitrile
AIDS=acquired immune deficiency syndrome
Alloc or alloc=allyloxycarbonyl
ARC=AIDS related complex
BOC or Boc=t-butyloxycarbonyl
DMF=dimethylformamide
DSC=differential scanning calorimetry
EDC=1-ethyl-3-(3-dimethylaminopropyl)carbodiimide
Et=ethyl
HIV=human immunodeficiency virus
HOBT or HOBt=1-hydroxy benzotriazole hydrate
HPLC=high performance liquid chromatography
IPAc=isopropyl acetate
IPA=isopropyl alcohol
KF=Karl Fisher titration for water
LC=liquid chromatography
LHMDS=lithium hexamethyldisilazide
Me=methyl
MeOH=methanol
MSA=methanesulfonic acid
MTBE=methyl tert-butyl ether
NCS=N-chlorosuccinimide
NMR=nuclear magnetic resonance
NSA=naphthalenesuflonic acid
OTf=triflate
PPA=polyphosphoric acid
i-Pr=isopropyl
TBDC=di t-butyl dicarbonate
TEA=triethylamine
TGA=thermogravimetric analysis
THF=tetrahydrofuran
XRPD=x-ray powder diffraction The following examples serve only to illustrate the invention and its practice. The examples are not to be construed as limitations on the scope or spirit of the invention.

EXAMPLE 1

3-Methoxy-5-bromopyridine (2)

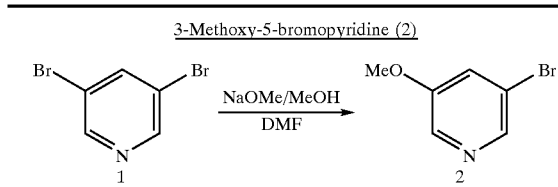

| Material | MW (g/mol) | Amount | mmol |
|---|---|---|---|
| Dibromopyridine 1, 98% | 236.89 | 48.34 g | 200 |
| Bromomethoxypyridine 2 | 188.02 | | |

-continued

3-Methoxy-5-bromopyridine (2)

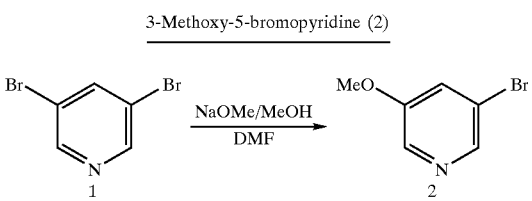

| Material | MW (g/mol) | Amount | mmol |
|---|---|---|---|
| 25 wt % NaOMe/MeOH (d = 0.945) | 54.02 | 56 mL | 240 |
| DMF | | 48 mL | |
| 20% Sodium chloride | | 420 mL | |
| Methyl-t-butyl ether | | 300 mL | |
| Water | | 120 mL | |

To a 500 mL flask equipped with condenser for distillation was charged 48.34 g dibromopyridine (200 mmol), 56 mL of 25 wt % NaOMe/CH$_3$OH (240 mmol) and 48 mL DMF. The mixture was heated to 90° C. A clear solution formed, which then turned cloudy. The mixture was aged 4 h at 90° C. and 3 h at 100° C. HPLC assay showed that the reaction was complete (<0.1 A % of 1). Some solvent was distilled out continuously during the age to maintain the internal temperature. The mixture was cooled to 18° C. and 60 mL water and 60 mL 20% NaCl were added. After 1 min, 300 mL MTBE was added. The mixture was agitated for 5 min and was transferred to a separatory funnel. After settling, the bottom aqueous layer was cut and the organic was washed with 3×120 mL 20% NaCl, then 60 mL water. The assay yield of bromomethoxypyridine 2 was 88% as determined by HPLC. $^1$H NMR (CDCl$_3$, 500 Hz): δ 8.30 (s, 1H), 8.25 (d, J=2.3 Hz, 1H), 7.37–7.38 (m, 1H), 3.87 (s, 3H).

| HPLC Assay: | |
|---|---|
| Column: | Zorbax RX-C8 (4.6 mm × 250 mm) |
| Solvents: | 60% CH$_3$CN, 40% 0.1% H$_3$PO$_4$ |
| Flow: | 1.0 mL/min |
| Sample volume: | 10 μL |
| Wavelength: | 210 nm |
| Retention times: | |
| The tarry impurity | 2.1 min |
| Dimethoxypyridine | 2.4 min |
| DMF | 2.7 min |
| Bromomethoxypyridine 2 | 4.9 min |
| Dibromopyridine 1 | 6.2 min |

EXAMPLE 2

3-Methoxy-5-(t-butyloxycarbonylaminomethylcarbonyl)-pyridine (5)

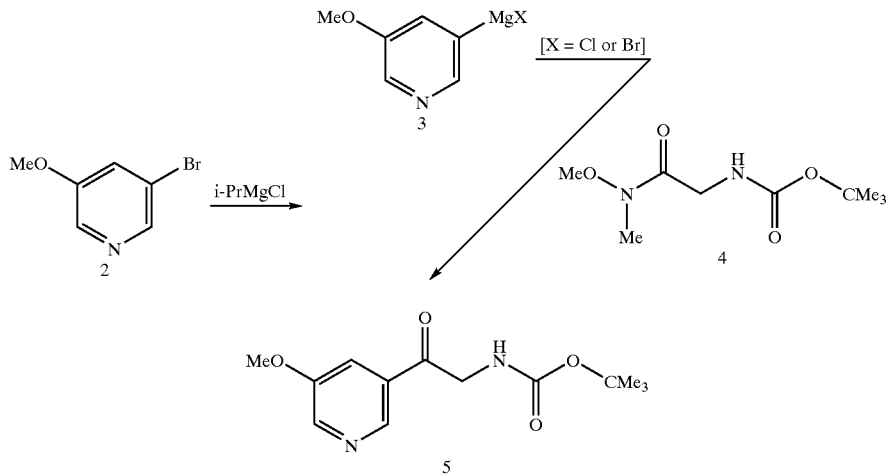

| Material | MW (g/mol) | Amount | moles |
|---|---|---|---|
| Bromomethoxypyridine 2 | 188.02 | | 18.9 |
| BOC-Aminoketone 5 | 266.29 | | |
| iso-Propylmagnesium chloride/THF | | 17.6 L | 35.2 |
| Weinreb amide 4, 96.3 wt % | 218.26 | 3.44 Kg | 15.19 |
| Tetrahydrofuran | | 114 L | |
| Isopropyl acetate | | 92 L | |
| n-Heptane | | 45 L | |
| 37% Hydrochloric acid | | 3.48 Kg | 35.2 |
| Water | | 82 L | |

A solution of 2 in MTBE was concentrated in a 100 L flask to 23 L by vacuum distillation at <40° C. About 91 L of dry THF was added slowly during distillation to solvent switch to THF and to dry the solution. The final THF solution (23 L, 18.9 mol 2) was charged into a 50 L flask, and the flask was degassed and then placed under a nitrogen atmosphere. After cooling over an ice bath, 10.4 L 2M iso-PrMgCl/THF was added over 21 min at <24° C. to afford a cloudy mixture. The mixture was aged 2 h at 20–30° C. at which point HPLC assay showed 2 at 1.0 A %. The reaction mixture after 1 h age was a clear, dark brown solution. The Grignard solution 3 was held 3 h more before its use.

In another 100 L flask, 3.44 kg Weinreb amide (15.19 mol) was mixed with 23 L dry THF. The cloudy solution was degassed and placed under an inert nitrogen atmosphere. The solution was cooled to −21° C. to give a slurry to which was added 7.2 L 2M i-PrMgCl/THF over 30 min at <−10° C. A nearly clear gray solution formed, to which the Grignard solution 3 was added over 30 minutes at <−11+ C. The gummy precipitate that formed in the Grignard solution was not soluble in THF and was not transferred. The mixture was warmed to 24° C. over 1 h and the resulting dark red solution was aged 15 h at 15–24° C. HPLC assay showed that the reaction complete (<1 A % Weinreb amide 4). The dark reddish-brown mixture was cooled to 9° C., and 23 L dilute aqueous HCl (prepared using 3.48 kg of 37 wt % HCl) was added with vigorous agitation at <35° C. The mixture was agitated for 5 min, transferred to an 100 L extractor, allowed to settle, and the bottom aqueous layer (pH 7–8) was cut. The organic layer was transferred back to the 100 L flask where it was batch concentrated to 55 L at <40° C. and flushed with 90 L of IPAc to solvent switch. The final solution concentrate (~55 L) was cooled to room temperature and diluted with 23 L water. The mixture was transferred to a 100 L extractor, allowed to settle, and the aqueous layer was cut. The organic layer was washed with 2×23 L and 1×16 water. The organic layer was batch concentrated at <35° C. in a 72 L flask. The final concentration to 13 L was done at <60° C. The mixture was then heated to 64° C. to form a clear solution, then cooled to 58° C. at which point 3 g of seed crystals of 5 were added. A slurry formed at 55° C. The slurry was cooled to 25° C., 39 L of n-heptane was added over 40 min, and the slurry was aged 15 h at room temperature and then 2 h at 0–5° C. The solids were filtered, rinsed with 8 L 3:1 n-heptane/IPAc and dried in a vacuum oven at 50° C. to afford 3.61 Kg of 5 as a yellowish crystalline solid (87% yield based on 4, 99.7 A % and 97.3 wt % purity).

$^1$H NMR (CDCl$_3$, 500 Hz): δ 8.77 (s, 1H), 8.53 (d, J=2.8 Hz, 1H), 7.70–7.71 (m, 1H), 5.49 (broad s, 1H), 4.48 (d, J=4.1 Hz, 2H), 3.93 (s, 3H), 1.49 (s, 9H).

HPLC Assay:

| | |
|---|---|
| Column: | Zorbax RX-C8 (4.6 mm × 250 mm) |
| Solvents: | 60% CH$_3$CN, 40% 0.1% H$_3$PO$_4$ |
| Flow: | 1.0 mL/min |
| Sample volume: | 10 μL |
| Wavelength: | 210 nm |

EXAMPLE 3

-continued

Retention times:

| | |
|---|---|
| Methoxypyridine | 2.2 min |
| Dimethoxypyridine | 2.4 min |
| Weinreb amide 4 | 3.4 min |
| BOC-aminoketone 5 | 3.9 min |
| IPAc | 4.1 min |
| Bromomethoxypyridine 2 | 4.9 min |
| Impurity | 6.2 min |

3-Methoxy-5-(aminomethylcarbonyl)pyridine HCl salt

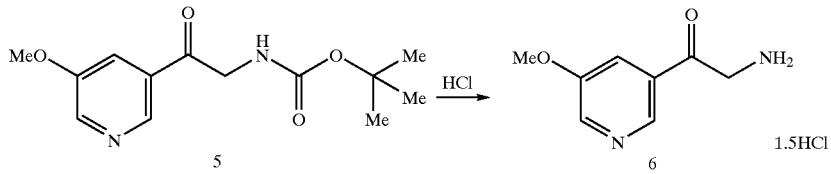

| Material | MW (g/mol) | Amount | moles |
|---|---|---|---|
| BOC-Aminoketone 5 | 266.29 | 2.19 Kg | 8.22 |
| 5N HCl | | 4.93 L | 24.6 |
| 5N NaOH | | 2.47 L | 12.3 |

To a 22 L round bottomed flask equipped with an overhead stirrer, thermocouple probe and nitrogen line was charged 4.93 L 5N HCl. The acid solution was warmed to 40° C. over a steam bath, after which 2.19 Kg of solid BOC-aminoketone 5 was added in portions over 20 min. After the addition, the reaction solution was aged 1.3 h at 40° C. Ice was then added to the bath to cool the batch to 15° C. and 2.47 L 5N NaOH was added over 50 min to neutralize the excess HCl. The resulting solution was cooled over salt/ice bath.

$^1$H NMR (D$_2$O, 500 Hz): δ 8.96 (s, 1H), 8.73 (d, J=2.5 Hz, 1H), 8.52–8.53 (m, 1H), 4.77 (s, 2H), 4.07 (s, 3H).

HPLC Assay:

| | |
|---|---|
| Column: | Zorbax RX-C8 (4.6 mm × 250 mm) |
| Gradient: | min  CH$_3$CN/0.1% H$_3$PO$_4$ |
| | 0    5/95 |
| | 12   90/10 |
| | 13   5/95 |
| Flow: | 1.0 mL/min |
| Sample volume: | 5 µL |
| Wavelength: | 210 nm |
| Retention times: | |
| Aminoketone 6 | 2.1 min |
| BOC-aminoketone 5 | 8.2 min |

EXAMPLE 4
4-(tert-butyloxycarbonyl)-2-(S)-((2,2,2-trifluoroethyl)aminocarbonyl) piperazine Step One: Preparation of the pyrazine amide

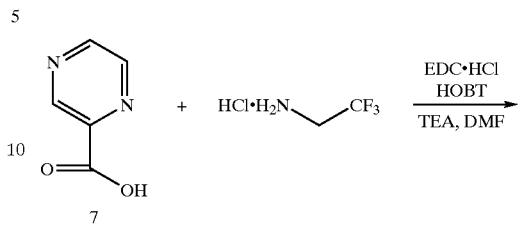

-continued

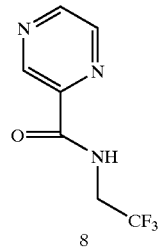

Pyrazine 2-carboxylic acid (1204 g) was suspended in DMF (4.8 L, 4 mL/g acid). 2,2,2-trifluoroethylamine.HCl (TFEA.HCl) (1200 g), 1-hydroxybenzotriazole (HOBT) (60 g) and triethylamine (TEA) (1410 mL) were then added sequentially (exotherm upon addition of TEA, flask cooled with ice bath and temperature kept below 35° C.). The reaction was cooled to 15° C. and 1-(3-dimethylaminopropyl)-3-ethylcarbodiimide.HCl (EDC.HCl) (1940 g) was added portionwise over 15–30 min. The reaction temperature was kept below 35° C. When the reaction appeared complete (approx. two hours, <5% pyrazine 2-carboxylic acid by LC assay), the reaction mixture (yellow/white slurry) was diluted with 10% K$_2$CO$_3$ in water (24 L, 20 mL/g acid) and the reaction slurry was kept below 35° C. The slurry was cooled to 10° C., aged for two hours and filtered (mother liquor assay=3–4 mg/mL). The wet cake was washed with deionized water (12 L, 10 mL/g acid) and dried under vacuum (22" Hg) at 40° C. with a nitrogen purge. Theoretical yield of 1816 g. Actual yield 1533 g (84%).

¹H NMR: (CD₃CN, 400 MHz): δ 9.29 (d, J=1.5 Hz, 1H), 8.82 (d, J=2.5 Hz, 1H), 8.63 (dd, J=2.6, 1.4 Hz, 1H), 8.40 (bs, 1H), 4.14 (dq, J=9.4, 6.8 Hz, 2H). HPLC Assay conditions: Waters Xterra RP8 column, elution with acetonitrile and 5 mM K phosphate adjusted to pH=8, detection at 220 nm.

Step Two: Preparation of the piperazine amide

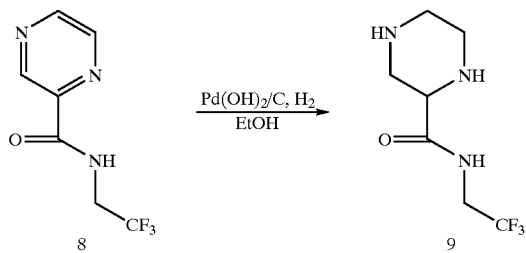

Pyrazine amide (60.2 g 0.268 mol, not corrected for water content) was suspended in absolute ethanol (550 mL) in a 1.0 L autoclave hydrogenation vessel and cooled to 15° C. Wet 20% Pd(OH)₂/C 11.0 g (20 wt %, 50 wt % wet) was added and reaction was purged with N₂ three times. H₂ (5 psig) was introduced with stirring and the temperature maintained at 15° C. for 60 minutes. The temperature was then increased to 60° C. and the hydrogen pressure increased to 40 psig and the reaction mixture stirred for 18 additional hours. The reaction was considered complete when conversion is >99% by LC assay. The reaction mixture was filtered through Solka-Floc and the catalyst solids were washed with ethanol 2×110 mL. Assay of the combined filtrate and washes gave 53.5 g of racemic piperazine amide (Yield=86%)

1H NMR (CD3CN, 400 MHz): δ 7.58 (bs, 1H), 3.90 (dq, J=9.5, 6.7 Hz, 2H), 3.24 (dd, J=7.9, 5.5 Hz, 1H), 2.96 (dd, J=12.1, 3.6 Hz, 1H), 2.84–2.78 (m, 1H), 2.77–2.67 (m, 3H), 2.66–2.56 (m, 1H), 1.90 (s, 2H). HPLC Assay conditions: YMC Basic column, elution with acetonitrile and 0.1% aqueous H₃PO₄, detection at 210 nm.

Step Three: Resolution of the piperazine amide

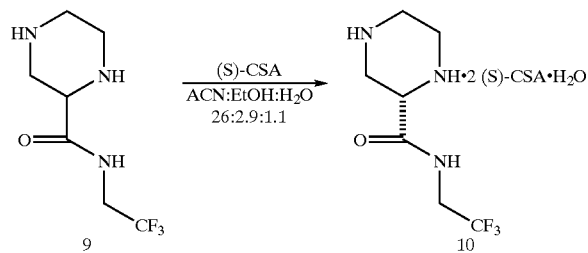

The pip amide ethanol filtrate (116.37 g containing 10.3 g of racemic pip amide by LC assay) was concentrated in vacuo to a final volume of 40.2 mL (3.9 mL per gram of pip amide) and the slurry is diluted with 82.4 mL (8 mL per gram pip amide) of acetonitrile (ACN) and stirred until homogenous. Separately (S)-camphorsulfonic acid (S)-CSA) (19.26 g, MW=232.30, 1.7 eq) was dissolved in 185 mL of ACN (18 mL per gram of pip amide). The water content of the two solutions was then determined by Karl Fisher titration. The CSA solution was added to the pip amide solution giving a small exotherm to approx. 31–32° C. Water (11.02 mL, 1.118 mL per gram of pip amide minus the total water content of the two solutions) was then added, such that the acetonitrile:ethanol:water ratio was 26:2.9:1.1 (v/v/v). Solids began to form after 15–30 min. The solution/slurry was heated to 72° C. to completely dissolve all solids. The yellow solution was recooled to 62° C. and seeded with a slurry of 10.3 mg of pip amide salt in 1 mL of acetonitrile. After a two hour age at 62° C. the slurry was allowed to cool to room temperature overnight (crystallization was complete when loss to mother liquors was <21 mg pip amide/mL by LC assay. The slurry was filtered then washed with 2×30 mL of ACN:EtOH:H₂O [(26:2.9:1.1), (v:v:v)] solution. The wet cake (~13 g, white solid) was dried at 40° C. in a vacuum oven (24 in Hg, nitrogen sweep) to give 11.16 g of product (yield=33%). Assay method (Pip Amide) as above. Chiral assay gives an enantiomeric excess (ee) of 98.0%.

1H NMR (CD₃OD, 400 MHz): d4.84 (bs, 5H), 4.64 (dd, J=12.0, 3.6 Hz, 1H), 4.13–3.94 (m, 3H), 3.77 (m, 2H), 3.66 (m, 1H), 3.54–3.43 (m, 2H), 3.28(d, J=14.7 Hz, 2H), 2.82 (d, 14.7 Hz, 2H), 2.55 (m, 2H), 2.36 (m, 2H), 2.12–1.998 (m, 4H), 1.92 (d, J=18.4 Hz, 2H), 1.72 (m, 2H), 1.45 (m, 2H), 1.09 (s, 6H), 0.87 (s, 6H). Enantiomeric excess determined by chiral HPLC of the mono BOC piperazine amide. HPLC assay conditions: Chiral AGP column, elution with acetonitrile and 10 mM Kphospate, pH=6.5, detection at 210 nm.

Step Four: Upgrade of ee of (S)-piperazine amide bis (S)-CSA salt

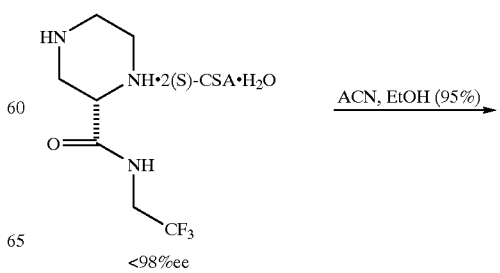

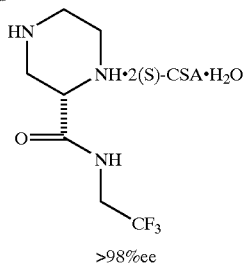

>98%ee

To a 12 L flask was charged (S)-pip amide salt (412.87 g) having an ee of less than 98%, 7.43 L of ACN and 825 mL of 190 proof EtOH. The slurry was heated to 75° C., aged for 1 hr at 75° C. (during heating the slurry thickened considerably), then allowed to cool to 25° C. overnight. The slurry was filtered and washed with EtOH (190 proof):ACN (10:90) (2×800 mL, 2 mL/g). The white solid was dried in a vacuum oven at 24 in Hg, 40° C. with a nitrogen sweep to give 400 g of product with an ee of 99%. Assays (normal and chiral) were performed as described above in the prior steps.

Step Five: Procedure for (S)-Mono BOC piperazine amide: BOC Protection

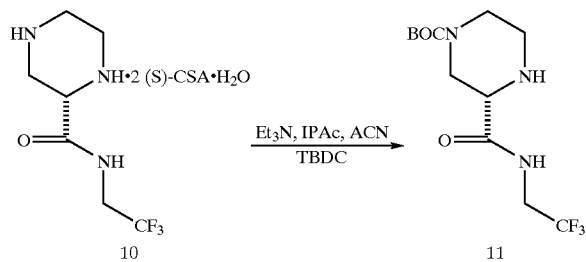

Bis (S)-CSA piperazine amide salt (20 g) was suspended in a mixture of 113 mL of isopropyl acetate (IPAc) and 57 mL of acetonitrile. Triethylamine (8.26 mL, 2 eq) was added and the mixture stirred until homogenous. A solution of di t-butyl dicarbonate (TBDC) (6.46 g, 1.0 eq) in a mixture of 20 mL isopropyl acetate and 10 mL of acetonitrile (ACN) was then added over 10 minutes. After aging for two hours the solution was assayed as necessary by LC (Pip Amide Assay, see above) until the reaction was complete (i.e., less than 5% starting material). When the reaction was complete, 100 mL of water and 135 mL of isopropyl acetate were added, the resulting layers were separated and the organic layer was concentrated to 28 mL. The residue was then diluted with 28 mL of isopropyl alcohol and reconcentrated to 28 mL. This was repeated two additional times. The yield of BOC pip amide was 87% with a mono:bis BOC ratio of 95:5, as determined by HPLC.

$^1$H NMR (CDCl$_3$, 400 MHz): δ=7.39 (app t, J=6.3 Hz, 1H), 3.96 (dd, J=3.5, 13.4 Hz, 1H), 3.88 (m, 2H), 3.67 (d, J=11.5Hz, 1H), 3.39 (dd, J=3.8, 8.6 Hz, 1H), 3.13 (dd, J=8.6, 13.3 Hz, 1H), 3.02 (br, 1H), 2.91 (m, 1H), 2.77 (m, 1H), 1.43 (s, 9H). $^{13}$C NMR (CDCl$_3$,) δ=171.43, 154.41, 123.89 (q, J=78.5 Hz), 80.16, 57.65, 43.63, 45.6 (br), 44.0 (br), 40.20 (q, J=34.7 Hz), 28.19. HPLC Assay conditions: YMC Basic column, elution with acetonitrile and 0.1% aqueous H$_3$PO$_4$, detection at 210 nm.

EXAMPLE 5

| Boc Alloc Piperazine 12 | | | |

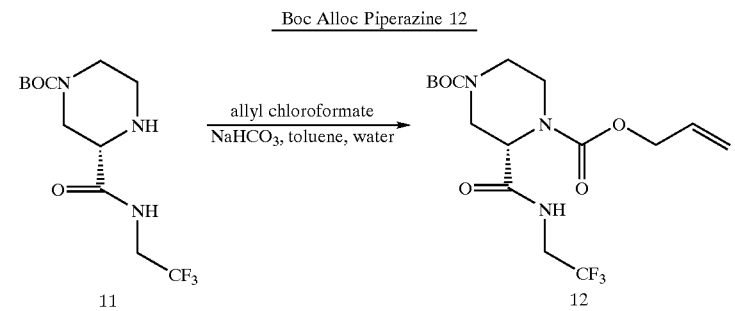

| Material | MW (g/mol) | Amount | moles |
|---|---|---|---|
| Boc piperazine 11 (34% soln. in IPA) | 311.3 | 15 Kg | 16.1 |
| Toluene (flush) | | 38 L | |
| Toluene (solvent) | | 33 L | |
| Water | | 32.2 L | |
| NaHCO$_3$ | 84 | 1.8 Kg | 21.4 |
| Allyl Chloroformate | 120.5 | 2.2 Kg | 18.5 |
| NaCl | | 360 grams | |

To a 100 L batch concentrator equipped with condenser for distillation was charged 15 Kg of Boc piperazine 11 (34% soln.) and 38 L toluene. The solution was distilled under vacuum (40 C, 20 mm Hg) to solvent switch EPA for toluene. Expected distillate is 37 Kg or 44 L of mixed solvent. The vessel was then set for reaction and 33 L toluene (solvent), 25 L water, and 1.8 Kg $NaHCO_3$ were added. The batch was cooled to 15 C and with vigorous mixing allyl chloroformate (18.5 L) was added by addition funnel at a rate to maintain batch temperature between 15–20° C. The reaction was mildly exothermic and reached about 20° C. by the end of the addition and remained at about that temperature for the duration of the reaction. When the reaction was complete as determined by HPLC, the agitation was stopped and the layers separated. The organic layer was washed with a solution of 360 grams NaCl in 7.2 L water.

Concentrated HCl (3.2 L) was added to a vigorously stirred solution of boc alloc piperazine 12 in toluene and the mixture was heated to 40° C. When the reaction was complete (in 1–2 hours as determined by HPLC), the reaction mixture was cooled to room temperature, and then water (33 L) was added. The batch was then cooled to 15° C. and THF (27 L) was added while maintaining the temperature at below 20° C. $Na_2CO_3$ (3.4 Kg) was then added in portions as it dissolved, followed by addition of NaCl (4.9 kg) to separate the organic from the aqueous layer. The organic layer was saved and the water layer was extracted a second time with THF (27 L).

$^1$H NMR ($CDCl_3$, 400 MHz) 5.95 (m, 1H), 5.35 (d, 1H), 5.28 (d, 1H), 4.75 (s, 1H), 4.68 (d, 1H), 4.53 (d, 1H), 3.90 (m, 3H), 3.20 (dd, 1H), 3.00 (m, 1H), 1.45 (s, 9H).

$^1$H NMR ($CDCl_3$, 400 MHz) 7.28 (s, 1H), 4.00 (dd, 1H), 3.97 (m, 2H), 4.70 (s, 1H), 3.40 (dd, 1H), 3.20 (dd, 1H), 3.05 (s, 1H), 2.93 (d, 1H), 2.81 (t, 1H), 1.80 (s, 1H), 1.43 (s, 9H).

EXAMPLE 6

Alloc Piperazine 13

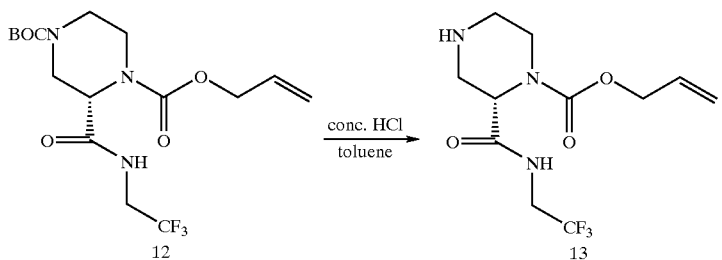

| Material | MW (g/mol) | Amount | moles |
|---|---|---|---|
| Boc alloc piperazine 12 | 395.4 | approx. 34 kg solution | 16.1 |
| Conc. HCl | | 3.2 L | 38.4 |
| Water | | 38 L | |
| THF | | 54 L | |
| $Na_2CO_3$ | 106 | 3.4 Kg | 32.1 |
| NaCl | | 4.9 Kg | |

EXAMPLE 7

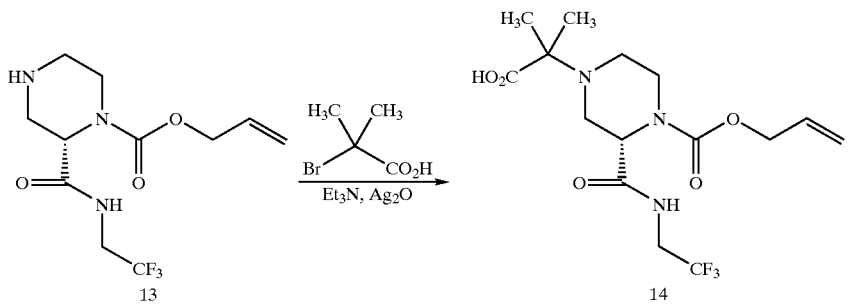

Piperazine Acid 14

| Material | MW (g/mol) | Amount | moles |
|---|---|---|---|
| Alloc piperazine 13 | 295.26 | 4.31 Kg | 14.6 |
| 2-bromo-2-methyl-propionic acid | 167.0 | 2.92 Kg | 17.5 |
| triethylamine | 101.19 | 8.14 L | 58.4 |
| Solka-floc | | 3 Kg | |
| Silver oxide | 232 | 1.87 Kg | 8.06 |
| Toluene | | 44 L | |
| 6N HCl | | 38.4 L | |
| 2N HCl | | 39 L | |

To a 100 L batch concentrator equipped with a condenser for distillation was charged alloc piperazine 13 (4.31 Kg, approximately a 7% solution in THF). The solution was distilled under vacuum to solvent switch THF for toluene while azeotroping residual water, after which a 100 L round bottomed flask was charged with the toluene solution and diluted with further toluene to a 10% solution. 2-bromo-2-methylpropionic acid (2.92 Kg) was then added, and the mixture was stirred until all material went into solution. Triethylamine (8.14 L) was then added followed by Solka-floc (2.97 Kg). The mixture was cooled while stirring with an ice water bath to 10° C., and then silver oxide was added in portions while maintaining the exothermic reaction at less than 40° C. After completion of the reaction (approximately one hour, as determined by HPLC), the reaction mixture was cooled with an ice bath and 6N HCl (38.4 L) was added in portions while maintaining the exothermic reaction at less than 50° C. The mixture was stirred for about ten minutes and filtered through a bed of Solka-floc. The filter cake was washed with 2N HCl (3×13 L). Further product was obtained from the combined filtrate and washings by cooling and separating the layers, adjusting the pH of the separated aqueous layer to 2 with aqueous NaOH, washing the layer with MTBE, separating the layers, adjusting the pH of the aqueous layer to 10 with aqueous NaOH, washing the layer with IPAc, separating the layers and adjusting the pH of the aqueous layer to 6 with 2N HCl, adding NaCl, and extracting the aqueous layer with THF.

$^1$H NMR (CDCl$_3$, 400 MHz): δ 9.02 (broad s, 1H), 6.98 (broad s, 1H), 5.90–6.00 (m, 1H), 5.24–5.28 (m, 2H), 5.65 (broad s, 1H), 4.16 (broad s, 1H), 2.90–2.93 (m, 1H), 2.55–2.57 (m, 1H), 2.40–2.41 (m, 1H), 1.59–1.61 (m, 1H).

EXAMPLE 8

4-[1-[5-(5-methoxy-3-pyridinyl)-carbonylmethylaminocarbonyl]-1-methylethyl]-2(S)-
[(2,2,2-trifluoroethyl)aminocarbonyl]-1-[allyloxycarbonyl]piperazine, bis sulfate 15

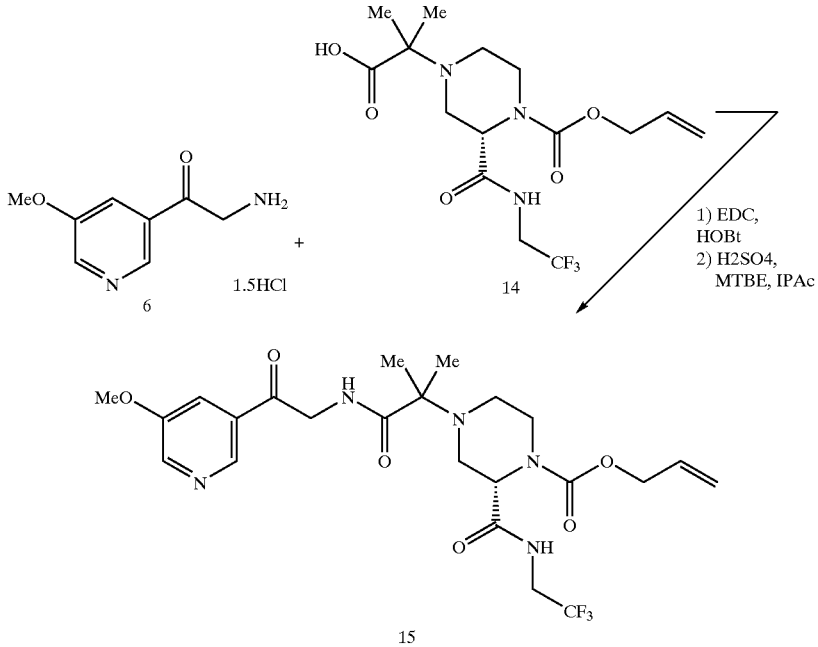

| Material | MW (g/mol) | Amount | moles |
|---|---|---|---|
| Aminoketone solution 6 | | | 8.22 |
| Piperazine Acid 14 | 381.35 | 3.13 Kg | 8.22 |
| Tetrahydrofuran | | 15 L | |
| Dimethylformamide | | 12.5 L | |
| HOBt | 135.13 | 1.22 Kg | 9.04 |
| EDC | 191.71 | 1.73 Kg | 9.04 |
| Diisopropylethylamine | 129.25 | 4.29 L | 24.6 |
| Ethyl Acetate | | 25 L | |
| Sat'd NaHCO₃ | | 12.5 L | |
| Water | | 13 L | |
| Isopropyl Acetate | | 100 L | |
| Sulfuric Acid (96 wt %, d = 1.84) | 98.08 | 0.786 L | 14.2 |
| MTBE | | 42 L | |

A 100 L round bottomed flask was fitted with a batch concentrator and 16.75 Kg solution (18.7 wt %, 8.22 mol) of piperazine acid 14 in THF was charged and batch concentrated. The solution was flushed with 2×7.5 L THF to dryness and was concentrated to a minimum volume. DMF (12.5 L) was added and residual THF was distilled at <25° C. HOBT hydrate (1.22 Kg) was added and allowed to dissolve. The batch was cooled to 17° C., and then 1.73 Kg EDC was added over 10 min. The resulting solution was aged 2 h at 21° C. The solution was cooled over a salt/ice bath to 0° C. and aminoketone hydrochloride 6 solution at 4° C. was added rapidly, followed by a 0.4 L water rinse. Following an exotherm to 16° C. and cooling over 20 min to 10° C., 4.29 L Hunig's base was added rapidly. With continued cooling over ice, the reaction mixture was aged 2.5 h. The mixture was diluted with 25 L EtOAc, 12.5 L sat'd NaHCO₃ and 6.3 L water and was cooled and aged 30 min to form a slurry. The precipitated HOBT was filtered on a filter pot and the cake was rinsed with a mixture of 8 L water and 1 L EtOAc. The filtrate was pumped into a 100 L extractor, cooled to 7° C. and acidified to pH 5 with 3.1 L 5N HCl. The aqueous layer was allowed to settle 30 min and was separated and extracted with 13 L EtOAc (0.4% product loss to aqueous layer). The combined organic layer was washed with 12 L sat'd NaHCO₃ (0.2% loss) and then with 12 L water (0.1% loss). The washed organic layer was weighed and assayed to contain 3.7 Kg ketoamide 15 (86% yield). This solution was batch concentrated to a minimal volume in a 100 L round bottomed flask, flushed with 3×10 L IPAc to dry and solvent switched, filtered through a glass funnel and adjusted to 19 L in IPAc. The solution was diluted with 19 L MTBE.

A 22 L round bottomed flask was charged with 19 L MTBE and cooled over a salt/ice bath to 5° C. H₂SO₄ (0.786 L, 2 eq vs. ketoamide) was added over 20 min (exotherm to 13° C.). The 100 L round bottomed flask containing the ketoamide solution was fitted with a 5 L addition funnel, H₂SO₄/MTBE was pumped in portions to the funnel and added over 2 h. The slurry is filtered over a large filter pot, rinsed with 6 L 2:1 MTBE/IPAc and dried under nitrogen, then 2 days in a vacuum oven (40° C.) to afford 5.41 Kg bis-sulfate salt in 84% yield (67.8 wt % free base, 93.5 A %).

¹H NMR of free base (CDCl₃, 500 Hz): δ 8.80 (s, 1H), 8.52 –8.53 (m, 1H), 8.37 (broad s, 0.6H), 7.90 (Broad s, 0.4H), 7.70–7.71 (m, 1H), 6.70 (broad s, 1H), 5.94 (broad s, 1H), 5.27–5.41 (m, 2H), 4.87 (broad s, 1H), 4.82 (s, 1H), 4.67 (d, J=4.5 Hz, 2H), 4.57 (d, J=18.3 Hz, 1H), 4.05–4.14 (m, 2H), 3.92 (s, 3H), 3.66 (d, J=11.2 Hz, 1H), 3.20–3.30 (m, 1H), 2.90 (d, J=10.8 Hz, 1H), 2.45 (d, J=9.3 Hz, 1H), 2.35–2.37 (m, 1H), 1.28 (s, 6H).

| HPLC Assay: | |
|---|---|
| Column: | Zorbax RX-C8 (4.6 mm × 250 mm) |
| Gradient: | min  CH$_3$CN/0.1% H$_3$PO$_4$ |
| | 0     5/95 |
| | 12    90/10 |
| | 13    5/95 |
| Flow: | 1.0 mL/min |
| Sample volume: | 5 μL |
| Wavelength: | 210 nm |
| Retention times: | |
| HOBT | 4.8 min |
| Pyrazine dimer | 5.6 min |
| Piperazine acid 14 | 5.9 min |
| EtOAc | 6.3 min |
| Ketoamide 15 | 8.2 min |
| HOBT adduct | 11.1 min |

EXAMPLE 9

4-[1-[5-(5-methoxy-3-pyridinyl)-2-oxazolyl]-1-methylethyl]-2(S)-[(2,2,2-trifluoroethyl)aminocarbonyl]-piperazine 16

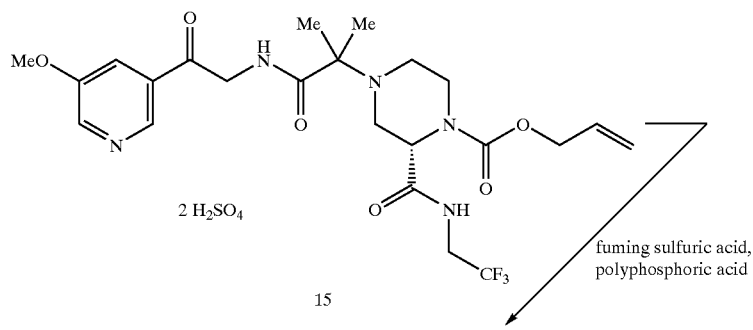

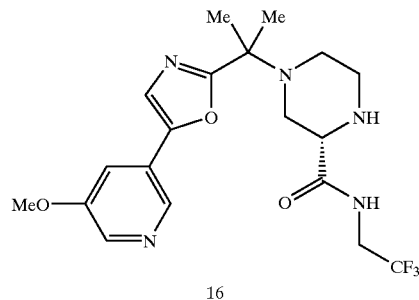

| Material | MW (g/mol) | Amount | moles |
|---|---|---|---|
| Ketoamide 15 (67.8 wt % free base) | 529.51 | 3.57 Kg | 6.74 |
| Polyphosphoric Acid | 342.04* | 7.67 Kg | 22.4 |
| 30% Oleum (26–29%) | | 8.95 Kg | |
| Water | | 32 L | |
| 50% NaOH | | 30 L | |
| IPAc | | 53 L | |
| Brine | | 16 L | |

*Estimated based on P$_4$O$_{10}$ equivalent.

To a 72 L round bottomed flask equipped with an overhead stirrer, thermocouple probe and nitrogen line was charged 8.95 L of 30% fuming sulfuric acid (oleum). The liquid was cooled over dry ice/acetone bath. When the temperature dropped to 9° C., crystallization of $SO_3$ was observed with concomitant exotherm to 11° C. Neat PPA (7.67 Kg viscous liquid) was then poured into the oleum over 1 h, avoiding the walls of glassware. A mild exotherm (−5° C.) was observed during addition. Ketoamide bis-sulfate salt 15 (5.26 Kg dusty powder) was added via funnel over 75 min at <20° C. to form a thick mixture with some undissolved ketoamide salt. The bath was drained and the mixture was heated over steam bath to 40–45° C. and aged 7 h to afford a homogeneous brown liquid. Reaction was complete as determined by HPLC assay. The reaction mixture was cooled over dry ice acetone bath to 3° C. and 22 L water was added slowly from an addition funnel to quench the reaction mixture, keeping the internal temperature <23° C. The solution was neutralized partially with 20 L 50% NaOH (<33° C.) and pumped into a 100 L Buchi reactor along with a 10 L water rinse, where it was adjusted to pH 1.7 with more 50% NaOH, diluted with 25 L IPAc, and then adjusted to pH 9.3 with 50% NaOH. The internal temperature was allowed to rise to 37° C. toward the end of addition to keep the salts solubilized. The two phases were separated and collected in polyjugs. Aqeuous loss was 0.2%. The Buchi vessel was thoroughly rinsed with water to remove gummy residues. The combined organic layer was washed with 16 L brine (0.04% loss) and 2 L water (0.2% loss). Assay yield was 2.44 Kg (85%) of title product 16 (90.4 A %, 95.1% ee).

$^1$H NMR (CDCl$_3$, 500 Hz): δ 8.63 (broad s, 1H), 8.50 (s, 1H), 8.28 (s, 1H), 7.36–7.37 (m, 1H), 7.34 (s, 1H), 3.91–4.00 (m, 2H), 3.94 (s, 3H), 3.78–3.79 (m, 1H), 3.02–3.11 (m, 4H), 2.88–2.91 (m, 1H), 2.65–2.73 (m, 2H), 1.60 (s, 3H), 1.59 (s, 3H).

| HPLC Assay: | |
|---|---|
| Column: | Zorbax RX-C8 (4.6 mm × 250 mm) |
| Gradient: | min    CH$_3$CN/0.1% H$_3$PO$_4$ |
| | 0    5/95 |
| | 12    90/10 |
| | 13    5/95 |
| Flow: | 1.0 mL/min |
| Sample volume: | 5 μL |
| Wavelength: | 210 nm |
| Retention times: | |
| Ketomaide 15 | 5.3 min |
| Biarylpiperazine 16 | 5.6 min |

EXAMPLE 10

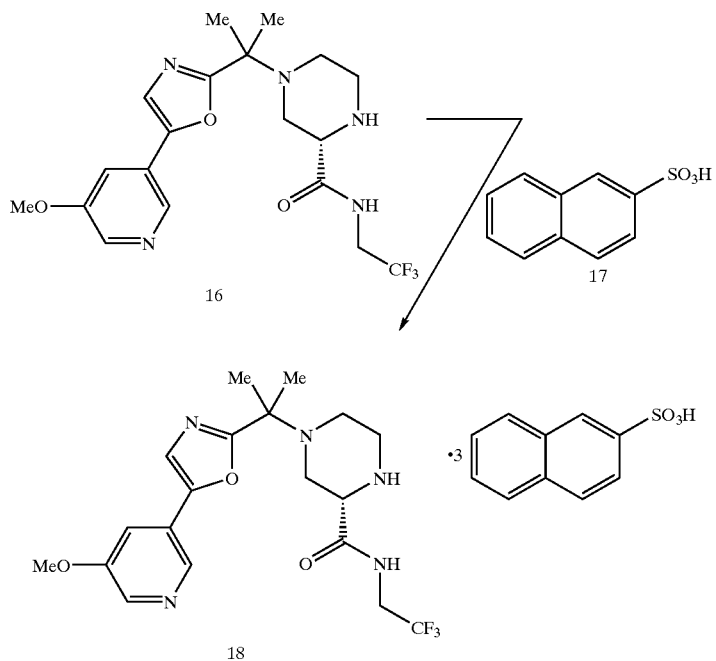

Tris-naphthalenesulfonic acid salt of 16

Part A — Purification of 2-Naphthalenesulfonic acid

| Run 1 — Material | MW (g/mol) | Amount | mmoles |
|---|---|---|---|
| 2-NSA 17 (76 wt % and 88A %) | 208.24 | 200 g | 730 |
| 2-NSA 17 seed | | 0.30 g | |
| Acetonitrile | | 800 mL | |

-continued

Tris-naphthalenesulfonic acid salt of 16

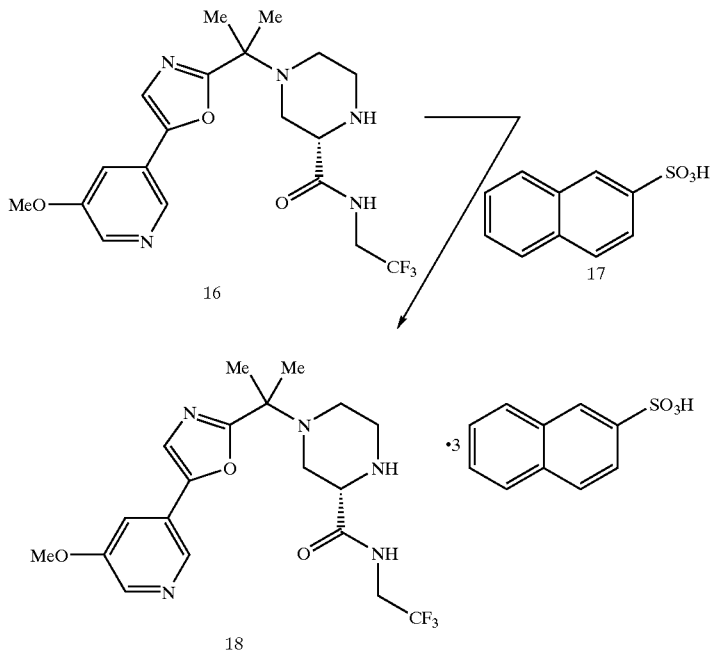

Part A — Purification of 2-Naphthalenesulfonic acid

| Run 1 — Material | MW (g/mol) | Amount | mmoles |
|---|---|---|---|
| Water |  | 10 mL |  |
| Toluene |  | 950 mL |  |

The impurities present in the crude 2-NSA 17 included 1-NSA, naphthalene, two isomers of naphthalenesulfone, and sulfuric acid. The crude 2-NSA 17 (200 g) was mixed with 400 mL CH$_3$CN, 10 mL water and 800 mL toluene and heated to 78–80° C. to dissolve the solids. The two layers were allowed to settle and the lower black layer (about 100 mL) was cut at 80° C. The top layer was cooled and seeded at 40° C. (100 mg seed). A slurry formed at −33° C. The slurry was cooled to 6° C., rinsed with 150 mL toluene and air dried in the funnel to afford 169 g of acid 17. In the black cut, most of 1-naphthalenesulfonic acid and sulfuric acid were rejected. In the mother liquor most of naphthalene and isomers of naphthalenesulfone are rejected. The purity of the filtered crystals was ~98.6 A %.

The crystals were mixed with 340 mL CH$_3$CN and heated to 50° C. to form a clear, gray solution, which was cooled and seeded at 40° C. (200 mg seed). A slurry formed at ~26° C. This was cooled to 5° C., filtered and rinsed with 100 mL CH$_3$CN to afford after drying in a vacuum oven at 60° C., 76.8 g solid (99.8 A %, 94.3 wt. % with 8% water, 48% recovery based on 76 wt % pure crude acid).

$^1$H NMR of 17 (DMSO-d6, δ) 8.17 (s, 1H), 7.98~7.96 (m, 1H), 7.91~7.90 (m, 1H), 7.88~7.86 (m, 1H), 7.73~7.71 (m, 1H), 7.53~7.51 (m, 2H), 6.98 (broad, 3H).

HPLC Assay:

| Column: | Zorbax RX-C8 (4.6 mm × 250 mm) |
|---|---|
| Solvents: | 50% CH$_3$CN, 50% 0.1% H$_3$PO$_4$ |
| Flow: | 1.0 mL/min |
| Sample volume: | 10 µL |
| Wavelength: | 210 nm |
| Retention times: |  |
| NSA isomer | 2.7 min |
| 2-NSA 17 | 3.1 min |
| Toluene | 10.4 min |
| Naphthalene | 13.5 min |
| Sulfone impurity #1 | 25.5 min |
| Sulfone impurity #2 | 29.2 min |

Run 2—

Crude 2-NSA 17 (40 g; from Rutgers Organic Corp.; 88 A % and 76.6 wt. % pure) was mixed with 80 mL of acetonitrile and 320 mL of toluene. The mixture was heated to about 80–82° C. to dissolve all of the solid. The mixture was maintained at temperature and allowed to settle and form two layers. The bottom black layer (13.3 g containing about 13.6% of the acid) was cut. Water (2 mL) was added to the top layer, the mixture agitated and then allowed to cool to room temperature resulting in the formation of a slurry which was aged at room temperature overnight. The slurry was filtered and rinsed with toluene (50 mL) to afford a gray solid, which was vacuum dried at 60° C. to give 27.55 g of solid (98.1 A % and 90.0 wt. % pure). Recovery was 80.8%. 6.5% of the acid was lost in the mother liquor.

Run 3—

Crude 2-NSA 17 (40 g; from Rutgers Organic Corp.; 88 A % and 76.6 wt. % pure) was mixed with 80 mL of acetonitrile and 240 mL of toluene. The mixture was heated to about 80–82° C. to dissolve all of the solid. The mixture was maintained at temperature and allowed to settle and form two layers. The bottom black layer (13.73 g containing about 14.6% of the acid) was cut. Water (30 mL) was added to the top layer, the mixture agitated and then allowed to cool to room temperature and to settle which resulted in the formation of 2 layers. The top layer most of the organic impurities was cut (0.4 wt. % of the acid was lost). The bottom layer was concentrated to about 60 mL by vacuum distillation at less than 50° C. Acetonitrile (570 mL) was then slowly added to remove the water by continuous distillation. The final volume was about 60 mL. Tolume (20 mL) was added and the mixture heated to 60° C. providing a clear solution, which was then cooled to 45° C. and seeded with 2-NSA seed crystals which resulted in the formation of a slurry which was cooled to about 0–5° C. and aged for 30 minutes. The slurry was then filtered and rinsed with toluene (30 mL) to afford an off-white solid. After vacuum drying at 60° C., a solid acid was obtained (20.9 g, HPLC: 99.5 A % and 96.7 wt. % pure). Recovery was 66%. 21.5% of the acid was lost in the mother liquor.

Part B - Preparation of the Tris-NSA salt of 16

| Material | MW (g/mol) | Amount | moles |
|---|---|---|---|
| Biarylpiperazine 16* | 427.42 | 2321 g | 5.43 |
| Seed of tris-salt 18 | 1052.14 | 12 g | |
| 2-Naphthalenesulfonic acid 17** | 208.24 | 3683 g | 16.29 |
| Acetonitrile | | 130 L | |
| Water | | 8.9 L | |

*15.3 wt % solution in $CH_3CN$, 94.8 ee %
**92.1 wt % and 99.8 A %

2-Naphthalenesulfonic acid 17 (92.1 wt % pure) was dissolved in 21 L of $CH_3CN$ and 8.82 L water at 65° C. A clear solution of biarylpiperazine 16 in $CH_3CN$ (15.17 kg, 2.321 kg free base 6) was added over 1 min along with 1 L $CH_3CN$ rinse. The mixture was still a clear solution (57° C.). After seeding (12 g), a slurry formed gradually. The slurry was aged 1h at 50–60° C. The slurry was vacuum distilled at 30–45° C. and 94 L $CH_3CN$ was added slowly to reduce the water content in order to lower the solubility of the tris-NSA salt 18. Samples were taken during distillation to monitor the change:

| Sample | Volume of $CH_3CN$ added | ee % of salt | Free base in supernatant | KF value of supernatant |
|---|---|---|---|---|
| #1 | 72 L | 99.9% | 3.25 g/L | 6.8% |
| #2 | 84 L | 99.8% | 2.53 g/L | 4.6% |
| #3 | 94 L | 98.2% | 1.48 g/L | 3.5% |

The volume was adjusted to ~49 L. The slurry was cooled to 25° C. and was aged overnight. The solids were filtered, rinsed with 12 L $CH_3CN$ and dried in a vacuum oven at 60° C. to afford 5.29 kg crystalline solid 18 (99.5 A %, 41.2 wt %, 98.1 ee %, 94% recovery or 97% after ee % correction.) Loss in the mother liquor was 2.6%.

$^1$H NMR of 18 (DMSO-d6, with two drops of D2O, δ) 9.27 (t, 1H, J=6.3 Hz), 8.65 (d, 1H, J=1.6 Hz), 8.42 (d, 1H, J=1.7 Hz), 8.13 (d, 3H, J=0.8 Hz), 7.96~7.94 (m, 3H), 7.91~7.89 (m, 5H), 7.88~7.85 (m, 3H), 7.72~7.69 (m, 3H), 7.53~7.51 (m, 6H), 4.03~3.97 (m, 3H), 3.93 (s, 3H), 3.33~3.24 (m, 2H), 3.02~2.96 (m, 2H), 2.50 ~2.45 (m, 2H), 1.56 (s, 6H).

HPLC Assay:

| Column: | Zorbax RX-C8 (4.6 mm × 250 mm) |
|---|---|
| Solvents: | 60% $CH_3CN$, 40% 0.1% $H_3PO_4$ |
| Flow: | 1.0 mL/min |
| Sample volume: | 10 μL |
| Wavelength: | 210 nm |
| Retention times: | |
| Biarylpiperazine 16 | 2.1 min |
| 2-NSA 17 | 3.1 min |

EXAMPLE 11

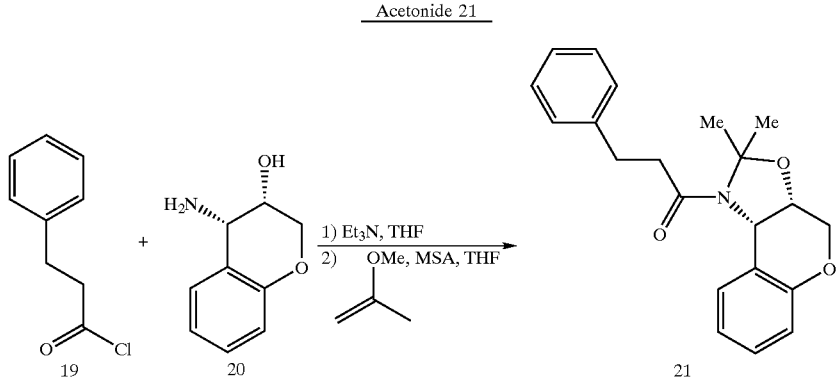

| Material | MW (g/mol) | Amount | mmoles |
|---|---|---|---|
| Aminochromanol 20 | 165.19 | 100.00 | 605 |
| Acetonide 21 | 337.41 | | |

-continued

Acetonide 21

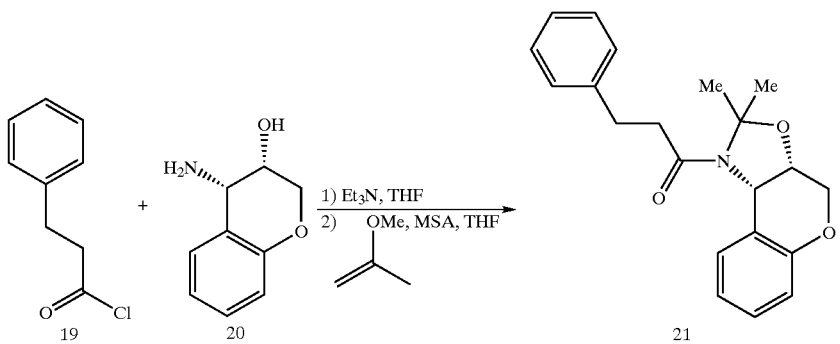

| Material | MW (g/mol) | Amount | mmoles |
|---|---|---|---|
| Triethylamine (d = 0.726) | 101.19 | 98 mL | 703 |
| Hydrocinnamoyl chloride* | 168.82 | 93 mL | 622 |
| 2-Methoxypropene (d = 0.753) | 72.11 | 232 mL | 2.42 |
| Methanesulfonic acid (d = 1.481) | 96.10 | 4.0 mL | 62 |
| THF | | 2000 mL | |
| IPAc | | 3000 mL | |
| 5% Sodium bicarbonate | | 1800 mL | |
| Cyclohexane | | 3850 mL | |
| Water | | 900 mL | |

*98%, d = 1.13

To a mixture of aminochromanol 20 (100.0 g, 95% ee, 605 mmol), TEA (89 mL, 635 mmol), and 1800 mL dry THF at room temperature was added a solution of hydrocinnamoyl chloride (93 mL, 622 mmol, 1.03 eq) in THF (200 mL) over 40 min, allowing the temperature to drift up to 45° C. At the end of the addition, a slurry was generated which was aged at 45° C. for 30 min then cooled to 30° C. 2-Methoxypropene (232 mL, 4.0 eq) was added, followed by 4.0 mL methanesulfonic acid (0.10 eq). The mixture was aged at 35~38° C. for 1 h. The flask was fitted with a condenser, and the slurry was warmed to 40° C., aged for 2 h, heated to 60° C. and aged at 60° C. under $N_2$ for 2~4 h until HPLC showed <0.1 A% amide remaining. The reaction was quenched with 9 mL triethylamine. The mixture was concentrated to about 2 L by vacuum distillation at <60° C. IPAc (3 L) was added slowly to replace THF. The final volume was 2.4 L. The mixture was cooled to room temperature and 900 mL of 5% $NaHCO_3$ were added to dissolve all solids. After settling, the aqueous layer was cut and the organic layer was washed with 900 mL 5% $NaHCO_3$ and then 900 mL water. The organic layer was concentrated to 2.5 L by vacuum distillation at <85° C., and cyclohexane (3.6 L) was added slowly during distillation to solvent switch. Some solids formed during distillation. When the mixture was heated to 70~75° C., most of the solids dissolved. At the end of distillation all solid was dissolved by heating to 75~80° C. The clear solution was cooled slowly to RT over 2.5 h during which slurry formed. This was aged 30 min at room temperature and 30 min at 0~5° C. The slurry was filtered and the solids were rinsed with 250 mL cyclohexane. After vacuum oven drying at 50° C., 184.16 g (98.7 A%, 98.1 wt% pure) of acetonide 21 was obtained. There was 6.4% loss in the mother liquor. The yield after purity correction was 88%.

$^1$H NMR (CDCl$_3$, 300 MHz) 7.25 (m, 7H), 6.82 (m, 2H), 4.70 (d, 1H), 4.33 (m, 1H), 4.08 (d, 1H), 3.92 (s, 1H), 3.11 (m, 2H), 2.92 (m, 1H), 2.68 (m, 1H), 1.61 (s, 3H), 1.23 (s, 3H).

| HPLC Assay: | |
|---|---|
| Column: | Zorbax RX-C8 (4.6 mm × 250 mm) |
| Solvents: | 60% CH$_3$CN, 40% 0.1% H$_3$PO$_4$ |
| Flow: | 1.0 mL/min |
| Sample volume: | 10 µL |
| Wavelength: | 210 nm |
| Retention times: | |
| Aminochromanol 20 | 2.1 min |
| Hydroxyamide | 3.9 min |
| IPAc | 4.1 min |
| Acetonide 21 | 7.7 min |
| Ester impurity | 11.1 min |

EXAMPLE 12

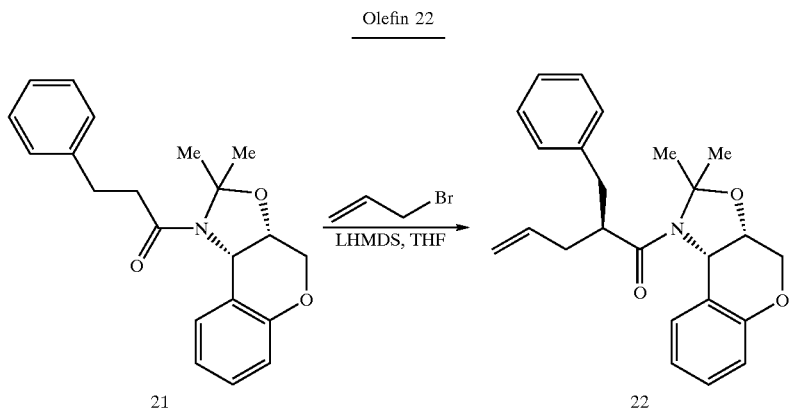

Olefin 22

| Material | MW (g/mol) | Amount | mmoles |
|---|---|---|---|
| Acetonide 21 (99.6 wt. %) | 337.41 | 50.00 g | 148 |
| Olefin 22 | 377.48 | | |
| Allylbromide | 120.98 | 18.60 g | 154 |
| 1.38M LHMDS in THF (d = 0.89) | | 109 g | 169 |
| Citric acid | 192.13 g/mol | 8.63 g | 44.9 |
| Tetrahydrofuran | | 343 mL | |
| Isopropyl acetate | | 1100 mL | |
| 0.3M Sulfuric acid | | 180 mL | |
| 5% Sodium bicarbonate | | 180 mL | |
| Water | | 180 mL | |

Acetonide 21 (50.00 g, 148 mol) was dissolved in 283 mL THF (KF=116 µg/mL). The solution was degassed and was placed under $N_2$. The solution was cooled to −46 to −44° C. and 18.60 g (1.04 eq) allylbromide was added. LHMDS/THF (107 g) was charged over 45 min at −46 to −44° C. After a 60 min age at this temperature, a sample was taken (quenched into 2 vol cold EPA) for HPLC assay, which showed 0.68 A % acetonide 21 remaining (99.3% conversion). More LHMDS/THF (2.14 g) was added, and the mixture was aged for 30 min more. HPLC showed 0.22 A % acetonide 21 (99.8% conversion). The reaction was quenched by adding cold citric acid solution in THF (8.63 g/60 mL THF). A slurry formed. The slurry was warmed from −32° C. to 16° C. over 1 h. The batch was vacuum distilled to ~400 mL at <40° C. and was flushed with 1100 mL IPAc to solvent switch to IPAc. The final volume was 450 mL. To the slurry was charged 180 mL 0.3 M $H_2SO_4$ (d=1.016 g/mL) at 20–25° C. All solids dissolved. After settling, the aqueous layer was cut and the organic layer was washed with 180 mL water and then 180 mL 5% $NaHCO_3$. The organic layer was diluted to 500 mL with IPAc. By HPLC the solution yield of olefin 22 was 98%. The concentration of olefin 22 was about 0.3 M. The solution was used in Example 13 without further purification.

$^1$H NMR (CDCl$_3$, 300 MHz) indicated a 5:1 mixture of rotamers: 7.30 (m, 5H), 7.05 (m, 1H), 6.80 (m, 1H), 6.4 (m, 1H), 5.85 (m, 1H), 5.15 (m, 1H), 4.98 (m, 1H), 4.40 (m, 1H), 4.25 (m, 2H), 3.38 (dd, 1H), 3.19 (m, 1H), 2.80 (m, 1H), 2.42 (m, 1H), 1.70 (s, 3H), 1.23 (s, 3H).

| HPLC Assay: | |
|---|---|
| Column: | Zorbax RX-C8 (4.6 mm × 250 mm) |
| Solvents: | 60% CH$_3$CN, 40% 0.1% H$_3$PO$_4$ |
| Flow: | 1.0 mL/min |
| Sample volume: | 10 µL |
| Wavelength: | 210 nm |
| Retention times: | |
| IPAc | 4.1 min |
| Allylbromide | 5.2 min |
| Acetone eliminated impurity | 6.0 min |
| Acetone adduct | 7.2 min |
| Acetonide 21 | 7.7 min |
| Olefin 22 | 12.6 min |
| Epi-olefin | 12.9 min |

EXAMPLE 13

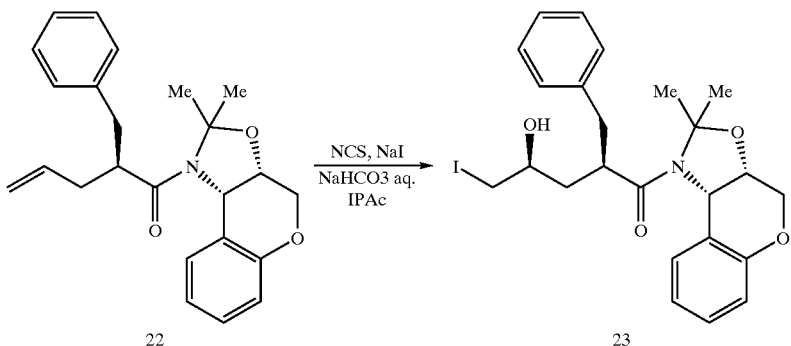

Iodohydrin 23

| Material | MW (g/mol) | Amount | mmoles |
|---|---|---|---|
| Olefin 22 | 377.48 | | ~148 |
| Iodohydrin 23 | 521.39 | | |
| NCS | 133.53 | 33.60 g | 252 |
| 57% NaI | 149.89 | 64.22 g | 244 |
| 20% Na thiosulfate pentahydrate | 248.18 | 165 mL | |
| IPAc | | ~50 mL | |
| 5% Sodium bicarbonate | | 220 mL | |
| Water | | 220 mL | |

To the solution of olefin 22 (500 mL, ~148 mmol) in IPAc was charged 220 mL water and 220 mL 5% NaHCO₃. The mixture was cooled to 3–4° C. NCS (33.60 g, 252 mmol, 1.7 eq) was added, then 57% NaI solution (64.22 g, 244 mmol, 1.65 eq) was added over 40 min at 4–7° C. The resulting brown solution was allowed to warm to 20° C. over 2 h and then was warmed to 30° C. over 15 min. The mixture was aged at 30° C. for 4 h. The conversion to iodohydrin was 98.6% after warming to 20° C. and 99.9% after 4 h age at 30° C. The batch was cooled to room temperature and then quenched with fast addition of 165 mL 20% $Na_2S_2O_3 \cdot 5H_2O$ (d=1.17 g/mL). After agitating for 2 min, the color of reaction mixture changed to orange from brown. The mixture was settled and the aqueous layer (650 mL) was cut. The organic layer (520 mL) was assayed and solution yield of iodohydrin was 83%. The solution was used in Example 14 without further purification.

$^1$H NMR (CDCl₃, 300 MHz) indicated a 5:2 mixture of rotamers: 7.30 (m, 5H), 7.05 (m, 1H), 6.82 (m, 1H), 6.60 (m, 1H), 5.92 (d, 0.3H), 5.58 (d, 0.7H), 4.45 (m, 2H), 4.20 (m, 2H), 3.63 (m, 1H), 3.44 (m, 2H), 3.20 (m, 2H), 2.82 (m, 2H), 2.40 (d, 1H), 2.00 (m, 1H), 1.72 (s, 3H), 1.49 (d, 2H), 1.29 (s, 3H).

| HPLC Assay: | |
|---|---|
| Column: | Zorbax RX-C8 (4.6 mm × 250 mm) |
| Solvents: | 60% CH₃CN, 40% 0.1% H₃PO₄ |
| Flow: | 1.0 mL/min |
| Sample volume: | 10 μL |
| Wavelength: | 210 nm |
| Retention times: | |
| IPAc | 4.1 min |
| Iodohydrin 23 | 9.3 min |
| Olefin 22 | 12.6 min |

EXAMPLE 14

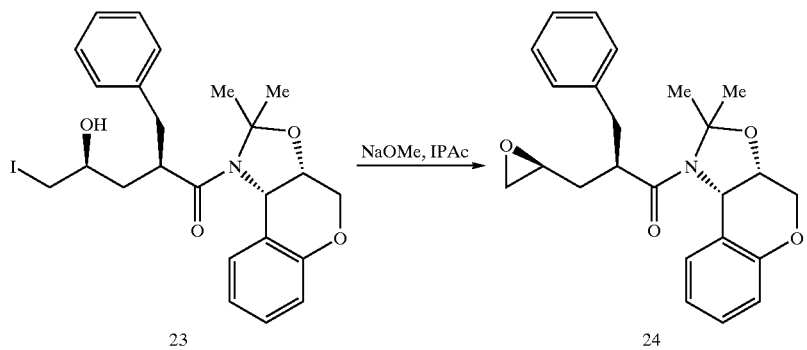

Epoxide 24

| Material | MW (g/mol) | Amount | mmoles |
|---|---|---|---|
| Iodohydrin 23 | 521.39 | | <148 |
| Epoxide 24 | 393.48 | | |
| 25% NaOMe in MeOH | 54.02 | 44.8 g | 207 |
| IPAc | | 500 mL | |
| IPA | | 450 mL | |
| 10% Sodium sulfate decahydrate | | 340 mL | |
| Water | | 170 mL | |

The solution of iodohydrin 23 in IPAc (520 mL, <148 mmol) was vacuum distilled at <35° C. IPAc (500 mL) was added slowly while the volume of solution was maintained at 500 mL. KF of the solution was <1400 μg/mL after the distillation. After azeotropic drying, the organic solution was cooled to 14–16° C. Then 44.8 g 25% NaOMe in methanol was added (small endotherm). The mixture was aged at 15° C. for 45 min. Sampling after 30 min age at 14–16° C. showed >99.7% conversion to epoxide. The reaction was quenched at 15–20° C. by adding 170 mL water. The mixture was agitated 2 min and settled 10 min. The aqueous layer was cut. The clear, dark brown organic layer was washed by 2×170 mL 10% $Na_2SO_4$-$10H_2O$ (d=1.04 g/mL). The pH of the first wash aqueous solution was 7 and was 6.5 for the second wash. The loss of epoxide in these two washes was <0.1%. The organic layer showed a lower 99.3% conversion to epoxide, due to some reverse reaction to iodohydrin. The organic layer was vacuum distilled to 220 mL and then flushed with 400 mL EPA at <45° C. A slurry was generated during this solvent switch. The slurry was heated rapidly to 80° C. to dissolve all solid. The dark solution was cooled slowly to 60~65° C. and was aged at this temperature to obtain a thin slurry. The slurry was cooled to room temperature over 1 h and was cooled to 0~5° C. for 3 h. The slurry was filtered and the cake was displacement-rinsed with 50 mL cold EPA. By HPLC there was 2.4% epoxide lost in mother liquor and rinse (160 mL). The cake was vacuum oven dried overnight at 40° C. with a nitrogen sweep to afford 48.02 g of epoxide 24 (99.4A % and 98.5 wt % pure). The yield was 81% from acetonide 21.

$^1$H NMR ($CDCl_3$, 300 MHz) indicated a 5:2 mixture of rotamers: 7.30 (m, 5H), 7.10 (m, 1H), 6.82 (m, 1H), 6.50 (m, 1H), 5.89 (d, 0.3H), 5.40 (d, 0.7H), 4.40 (m, 2H), 4.15 (m, 2H), 3.40 (m, 2H), 3.00 (m, 1H), 2.85 (m, 2H), 2.50 (dd, 0.7H), 2.40 (dd, 0.3H), 2.20 (m, 1H), 1.72 (s, 3H), 1.49 (d, 1H), 1.29 (s, 3H).

| HPLC Assay: | |
|---|---|
| Column: | Zorbax RX-C8 (4.6 mm × 250 mm) |
| Solvents: | 60% $CH_3CN$, 40% 0.1% $H_3PO_4$ |
| Flow: | 1.0 mL/min |
| Sample volume: | 10 μL |
| Wavelength: | 210 nm |
| Retention times: | |
| IPAc | 4.1 min |
| Epoxide 24 | 8.0 min |
| Iodohydrin 23 | 9.3 min |

EXAMPLE 15

Preparation of Penultimate 25

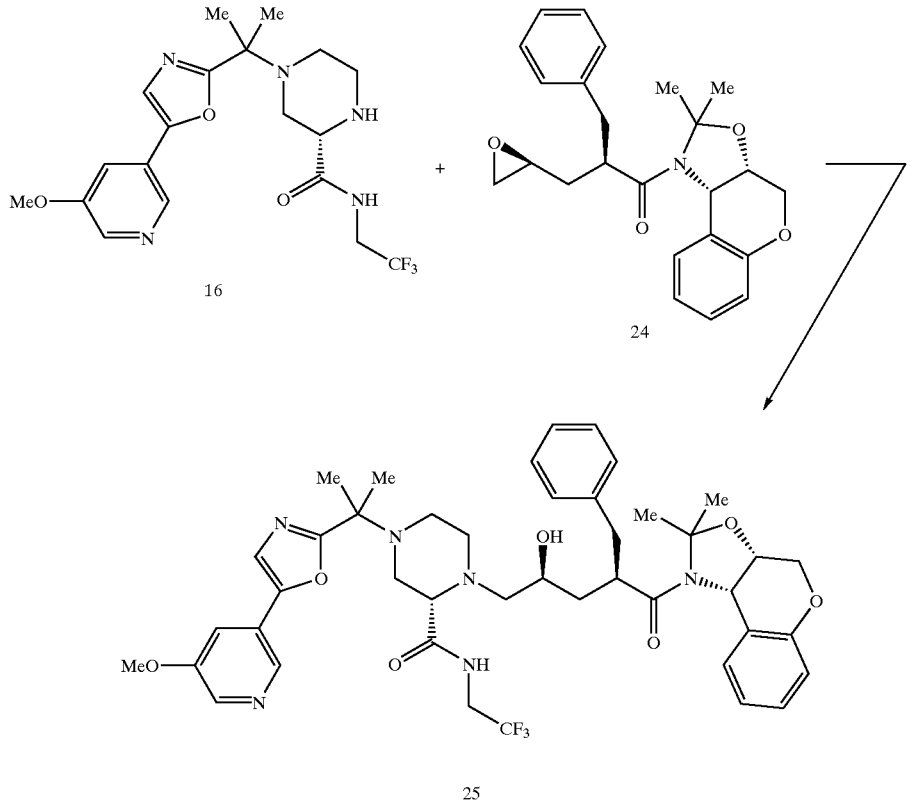

Biarylpiperazine tris-NSA salt (300.00 g, GMP) was slurried in MeOH (940 mL) and KOH in MeOH (860 mL, 1.0N). The slurry was allowed to stir for 4 h. MeOH was distilled off at 35 Torr with an internal temperature of 5° C. After ~800 mL was distilled off, the slurry became too thick to stir and toluene (1800 mL) was added. A total of 3600 mL of toluene was used to flush the slurry (mother liquors were checked for the presence of naphthalenesulfonic acid). The slurry was then filtered, rinsing 2×360 mL toluene. The filtrates were assayed by HPLC and found to contain 123.1 g biarylpiperazine. The filtrate was then concentrated and diluted with 480 mL t-amyl alcohol. It was concentrated again and then flushed with 450 mL t-amyl alcohol. It was assayed and found to contain 115.1 g biarylpiperazine. Epoxide 24 (107.00 g, 1.01 eq.) was added, and the mixture was stirred at 55° C. (internal temperature) for 90 h. The mixture was diluted with IPAc (1720 mL) and assayed for the coupled acetonide product 25 by HPLC (found 185.00 g (84% yield). Silica gel (370.0 g) and Darco G-60 activated carbon (46.25 g) were added and the mixture was heated at 50° C. for 1 hour. It was filtered through Solka Floc and rinsed with 925 mL 5% MeOH/IPAc (4×). The initial filtrate and first rinse were assayed and were found to contain a total of 146.03 g. Rinses 3 and 4 contained 24.69 g and 7.52 g, respectively. The filtrate, first and second rinses were combined. A portion of this containing ~100 g was chromatographed (16 cm column, 2.00 kg silica) using 0 to 6% MeOH/IPAc. Clean fractions were combined and concentrated.

$^1$H NMR (CD$_3$OD, 500 Hz): δ 8.48 (s, 1H), 8.23 (d, J=2.3 Hz, 1H), 7.64–7.65 (m, 1H), 7.63 (s, 1H), 7.20–7.32 (m, 5H), 7.01 (t, J=7.5 Hz, 1H), 6.68 (d, J=8.3 Hz, 1H), 6.45 (t, J=6.5 Hz, 1H), 6.35 (d, J=7.7 Hz, 1H), 5.67 (d, J=3.9 Hz, 1H), 4.45 (d, J=2.3 Hz, 1H), 4.32–4.35 (m, 1H), 4.18 (d, J=3.0 Hz, 1H), 3.93–4.00 (m, 1H), 3H), 3.95 (s, 3H), 3.77–3.85 (m, 2H), 3.43–3.48 (m, 1H), 3.27 (t, J=5.1 Hz, 1H), 3.03 (d, J=4.4 Hz, 1H), 2.73–2.83 (m, 2H), 2.55 (t, J=8.3 Hz, 1H), 2.34–2.43 (m, 3H), 1.93–1.98 (m, 1H), 1.66 (s, 3H), 1.52 (s, 6H), 1.14(s, 3H). LC-MS (M$^+$+1) (EI) 821.5.

EXAMPLE 16

(αR,γS,2S)-N-[(3S,4S)-3,4-dihydro-3-hydroxy-2H-1-benzopyran-4-yl]-γ-hydroxy-4-[1-[5-(5-methoxy-3-pyridinyl)-2-oxazolyl]-1-methylethyl]-α-(phenylmethyl)-2-[[(2,2,2-trifluoroethyl)amino]carbonyl]-1-piperazinepentanamide (Compound 26)

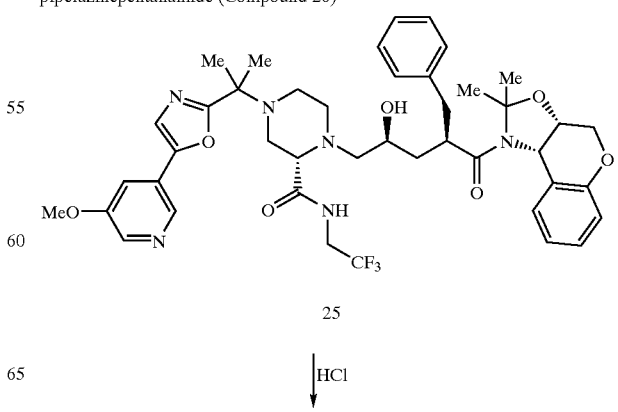

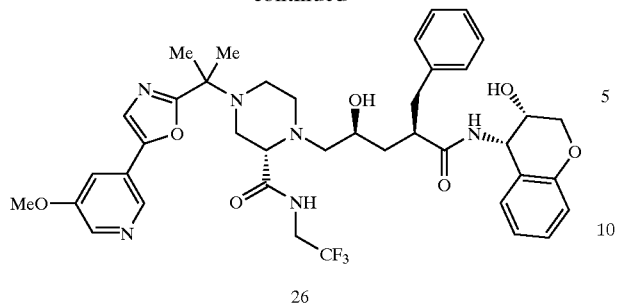

26

Compound 25 penultimate prepared in Example 15 (97.5 g) was dissolved in 225 mL MeOH and cooled to -10° C. 5.02N HCl in methanol (245 mL) was added dropwise over 30 min, keeping the temperature below 0° C. It was then transferred to a 0° C. bath. After stirring for 13 h, it was assayed and found to be greater than 98.5% complete. 5N NaOH (250 mL) was added, keeping the temperature below 0° C. After addition was complete the pH was checked and found to be 9. IPAc (1.0L) and water (200 mL) were added and the layers were shaken to dissolve a brown oil that formed during the quench. The layers were cut and the aqueous layer was assayed and found to contain 0.19 g of Compound 26. The organic layer was washed with 200 mL brine. The organic layer was assayed and found to contain 85.95 g of Compound 26 free base (92.7%). The brine layer was found to contain 0.05 g of Compound 26. Activated carbon (17.99 g) was added and the mixture was stirred at 50° C. for 1 h. After cooling to room temperature the slurry was filtered through solka-floc and the cake washed with IPAc, 3×180 mL. The filtrate and washes were combined and assayed which showed 80.54 g of Compound 26 free base. The combined filtrate and washes were then concentrated to a yellow foamy solid.

$^1$H NMR (CD$_3$OD, 500 Hz): δ 8.49 (s, 1H), 8.22 (d, J=1.6Hz, 1H), 7.66–7.67 (m, 1H), 7.20–7.25 (m, 4H), 7.14–7.17 (m, 1H), 7.06–7.10 (m, 2H), 6.80 (t, J=7.6 Hz, 1H), 6.71 (d, J=8.0 Hz, 1H), 5.13 (d, J=3.8 Hz, 1H), 4.04–4.06 (m, 2H), 3.92–3.98 (m, 1H), 3.94 (s, 3H), 3.78–3.82 (m, 1H), 3.72–3.77 (m, 2H), 3.06–3.10 (m, 1H), 2.96–3.03 (m, 2H), 2.88–2.94 (m, 1H), 2.85 (d, J=11.2 Hz, 1H), 2.70–2.77 (m, 2H), 2.63–2.67 (m, 1H), 2.44–2.50 (m, 1H), 2.34–2.44 (m, 4H), 2.00–2.04 (m, 1H), 1.60 (s, 3H), 1.59 (s, 3H), 1.35–1.38 (m, 1H). LC-MS (M$^+$+1) (EI) 781.5.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A process for preparing a piperazine of Formula (II):

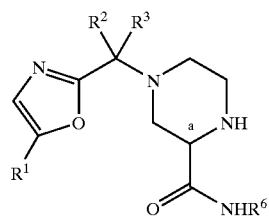

(II)

which comprises:
(A) treating a ketoamide of Formula (I):

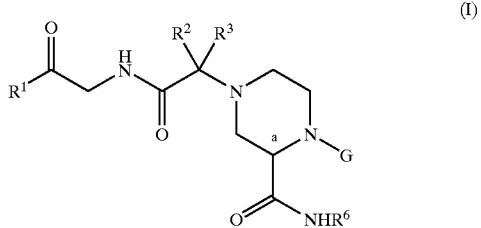

(I)

with fuming sulfuric acid in the presence of polyphosphoric acid to obtain the piperazine II; wherein stereocenter a is either in the R configuration or in the S configuration;
G is a nitrogen-protecting group;
R$^1$ is:

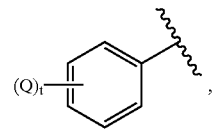

heterocycle, or substituted heterocycle;
wherein each Q is independently hydrogen, cyano, C$_1$–C$_4$ alkyl, or —O—C$_1$–C$_4$ alkyl;
heterocycle in R$^1$ is:

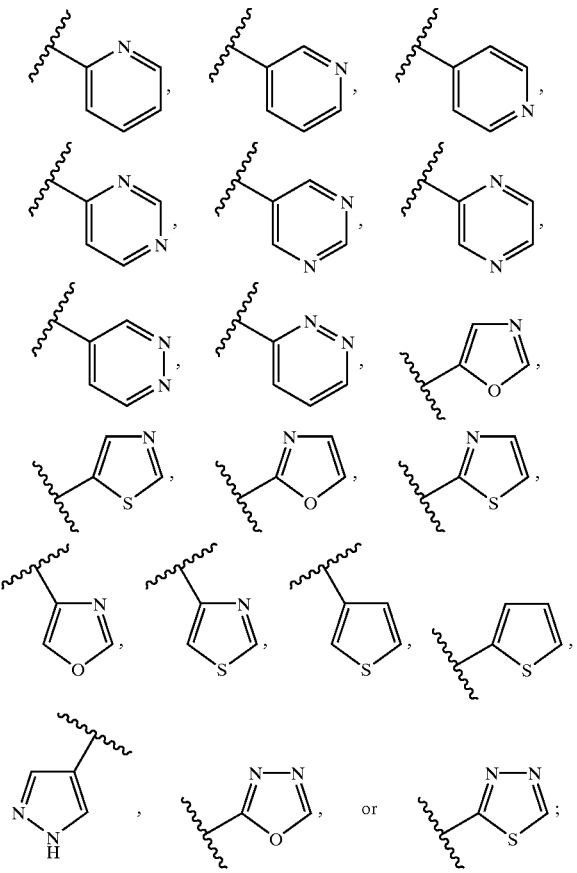

substituted heterocycle in R$^1$ is a heterocycle as defined above with one or more substituents independently selected from cyano, $C_1$–$C_4$ alkyl, —O—$C_1$–$C_4$ alkyl, S—($C_1$–$C_4$ alkyl), $NR^aR^b$, thiazolyl, oxazolyl, imidazolyl, pyrazolyl, triazolyl, pyrrolyl, isoxazolyl, and isothiazolyl;

$R^2$ and $R^3$ are each independently hydrogen, $C_1$–$C_6$ alkyl, or aryl, wherein the alkyl group is optionally substituted with one or more substituents each of which is independently halogen, —O—$C_1$–$C_6$ alkyl, or —O—$C_1$–$C_6$ haloalkyl; and wherein the aryl group is optionally substituted with one or more substituents each of which is independently halogen, —$C_1$–$C_6$ alkyl, —$C_1$–$C_6$ haloalkyl, —O—$C_1$–$C_6$ alkyl, or —O—$C_1$–$C_6$ haloalkyl; or $R^2$ and $R^3$ together with the carbon to which they are attached form $C_3$–$C_8$ cycloalkyl which is optionally substituted with one or more substituents each of which is independently halogen, —$C_1$–$C_6$ alkyl, —$C_1$–$C_6$ haloalkyl, —O—$C_1$–$C_6$ alkyl, —O—$C_1$–$C_6$ haloalkyl, or —$C_1$–$C_6$ alkyl substituted with —O—$C_1$–$C_6$ alkyl;

$R^6$ is —H or $C_1$–$C_6$ alkyl optionally substituted with one or more substituents each of which is independently
(1) halogen,
(2) —O—$C_1$–$C_6$ alkyl,
(3) —O—$C_1$–$C_6$ haloalkyl,
(4) —$C_1$–$C_6$ alkyl substituted with —$C_1$–$C_6$ alkyl,
(5) —$N(R^c)_2$,
(6) —$CO_2R^c$,
(7) —$N(R^c)(SO_2R^c)$,
(8) —C(=O)$R^c$, or
(9) —C(=O)—$N(R^c)_2$;

$R^a$ and $R^b$ are each independently —H or —$C_1$–$C_4$ alkyl; or alternatively $R^a$ and $R^b$ together with the nitrogen to which they are attached form $C_3$–$C_6$ azacycloalkyl;

each $R^c$ is independently —H or —$C_1$–$C_4$ alkyl; and t is an integer equal to zero, 1 or 2.

2. The process according to claim 1, wherein $R^1$ is pyridyl which is unsubstituted or substituted with 1 or 2 substituents each of which is $C_1$–$C_4$ alkyl or —O—$C_1$–$C_4$ alkyl.

3. The process according to claim 1, wherein $R^2$ and $R^3$ are either both —H or both methyl.

4. The process according to claim 1, wherein $R^6$ is

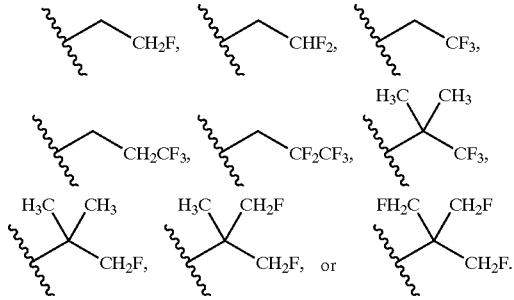

5. The process according to claim 4, wherein $R^6$ is

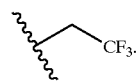

6. The process according to claim 1, wherein G is:

(1) ($C_1$–$C_8$ alkyl)oxycarbonyl, (2) allyloxycarbonyl, (3) benzyloxycarbonyl wherein benzyl is optionally substituted with from 1 to 3 substituents each of which is independently halogen, $C_1$–$C_4$ alkyl or —O—$C_1$–$C_4$ alkyl, (4) p-nitrobenzyloxycarbonyl, (5) phenyloxycarbonyl wherein phenyl is optionally substituted with from 1 to 3 substituents each of which is independently $C_1$–$C_4$ alkyl or —O—$C_1$–$C_4$ alkyl, or (6) methylcarbonyl wherein the methyl is optionally substituted with from 1 to 3 substituents each of which is independently chloro or fluoro.

7. The process according to claim 6, wherein G is allyloxycarbonyl.

8. The process according to claim 1, wherein the fuming sulfuric acid is employed in an amount in the range of from about 5 to about 20 equivalents and the polyphosphoric acid is employed in an amount in the range of from about 0.5 to about 10 equivalents per equivalent of ketoamide I.

9. The process according to claim 1, wherein the ratio of range from about 1:1 to about 30:1.

10. The process according to claim 1, wherein the acid treatment of ketoamide I is conducted at a temperature in the range of from about 0 to about 80° C.

11. The process according to claim 1, wherein treating Step A comprises forming the acid mixture by adding the polyphosphoric acid to the fuming sulfuric acid and then adding ketoamide I to the acid mixture.

12. The process according to claim 1, wherein the ketoamide I employed in the treatment step is a bis-sulfate salt of ketoamide I.

13. The process according to claim 1, which further comprises:

(X) forming a solution comprising the piperazine II product of Step A containing a minor portion of undesired optical isomer, 2-naphthalenesulfonic acid, and solvent; and (Y) crystallizing from the solution a crystalline 2-naphthalenesulfonic acid salt of II having enhanced optical purity.

14. A process for preparing Compound 16:

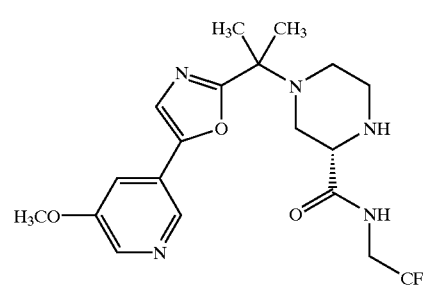

which comprises:

(aa) treating ketoamide 15:

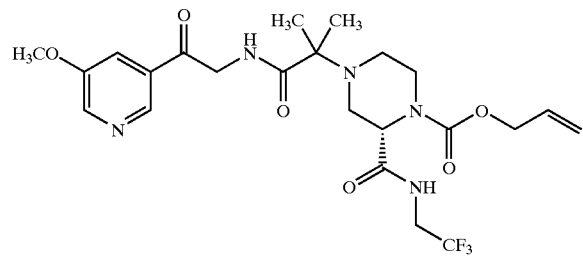

with fuming sulfuric acid in the presence of polyphosphoric acid to obtain Compound 16.

15. The process according to claim 14, wherein the process further comprises:

(xx) forming a solution comprising the Compound 16 product of Step (aa) containing a minor portion of its optical isomer, 2-naphthalenesulfonic acid, acetonitrile, and water;

(yy) crystallizing from the solution a crystalline tris-2-naphthalenesulfonate salt of 16 having enhanced optical purity.

* * * * *